(12) United States Patent
Kuwano et al.

(10) Patent No.: US 9,134,333 B2
(45) Date of Patent: *Sep. 15, 2015

(54) SAMPLE PROCESSING APPARATUS AND SAMPLE PROCESSING METHOD

(75) Inventors: Keisuke Kuwano, Kobe (JP); Daigo Fukuma, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 364 days.

This patent is subject to a terminal disclaimer.

(21) Appl. No.: 12/750,176

(22) Filed: Mar. 30, 2010

(65) Prior Publication Data

US 2010/0248292 A1  Sep. 30, 2010

(30) Foreign Application Priority Data

Mar. 31, 2009 (JP) ................................. 2009-087712

(51) Int. Cl.
| | |
|---|---|
| *C12Q 1/02* | (2006.01) |
| *C12M 1/26* | (2006.01) |
| *C12M 1/34* | (2006.01) |
| *G01N 35/02* | (2006.01) |
| *G01N 35/00* | (2006.01) |
| *G01N 35/04* | (2006.01) |

(52) U.S. Cl.
CPC ............ *G01N 35/02* (2013.01); *G01N 35/0092* (2013.01); *G01N 35/026* (2013.01); *G01N 2035/041* (2013.01)

(58) Field of Classification Search
CPC ....................................................... G01N 35/02
See application file for complete search history.

(56) References Cited

U.S. PATENT DOCUMENTS

| | | | | |
|---|---|---|---|---|
| 6,171,280 | B1 * | 1/2001 | Imazu et al. | ................... 604/118 |
| 8,161,831 | B2 * | 4/2012 | Fukuma | ..................... 73/864.21 |
| 8,594,836 | B2 * | 11/2013 | Hamada et al. | ................ 700/228 |
| 2005/0036913 | A1 | 2/2005 | Yamakawa et al. | |
| 2007/0110617 | A1 * | 5/2007 | Nagai et al. | ..................... 422/65 |

FOREIGN PATENT DOCUMENTS

| | | |
|---|---|---|
| JP | 05-072212 A | 3/1993 |
| JP | 2001-174468 | 6/2001 |
| JP | 2003-066050 | 3/2003 |
| JP | 2004-226065 | 8/2004 |

* cited by examiner

*Primary Examiner* — Scott Long
(74) *Attorney, Agent, or Firm* — Sughrue Mion, PLLC

(57) ABSTRACT

A sample processing apparatus comprising: an aspiration section for aspirating a sample from a sample container; a sample container take-out/returning section for taking out a sample container containing a sample from a sample rack holding a plurality of sample containers, and for returning the sample container, from which the sample has been aspirated, to the sample rack; a sample processing section for processing the aspirated sample; a transport section for transporting the sample rack to a take-out position for taking out the sample container from the sample rack; and a transport controller for controlling the transport section to transport the sample rack to a processing position for performing a predetermined process on another sample container held by the sample rack when one sample container has been taken out from the sample rack by the sample container take-out/returning section is disclosed. A sample processing method is also disclosed.

21 Claims, 25 Drawing Sheets

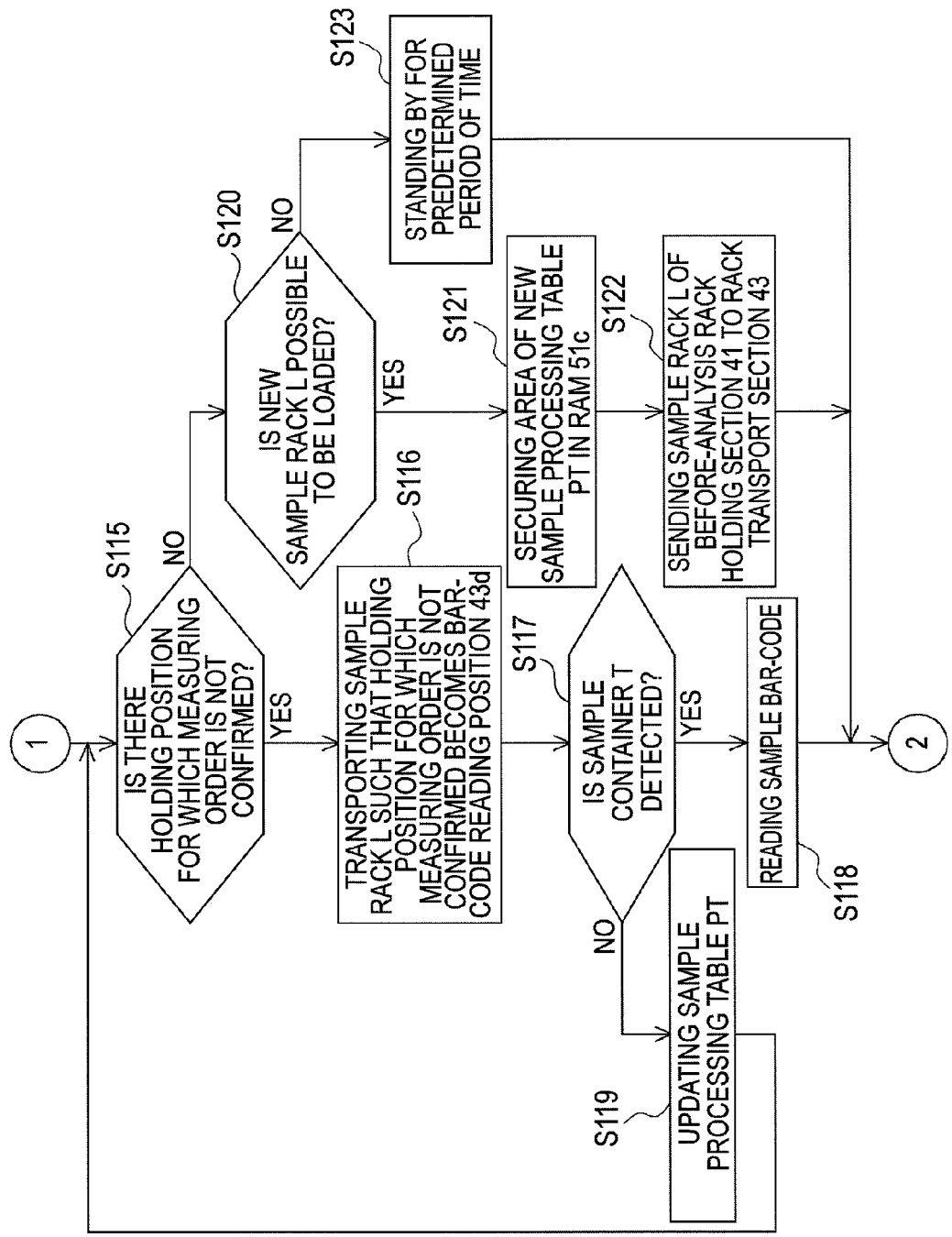

FIG.11

| HOLDING POSITION (F1) | EXISTENCE OF SAMPLE CONTAINER (F2) | MEASURING ORDER (F3) | MEASURING STATE (F4) |
|---|---|---|---|
| 1 | 1 | CBC+DIFF | MEASURED |
| 2 | 0 | NULL | NULL |
| 3 | 1 | CBC+DIFF | MEASURED |
| 4 | 1 | CBC+DIFF,NRBC | MEASURED |
| 5 | 1 | CBC+DIFF | UNMEASURED |
| 6 | 1 | CBC+DIFF,RET | UNMEASURED |
| 7 | 1 | CBC+DIFF | UNMEASURED |
| 8 | 1 | CBC+DIFF | UNMEASURED |
| 9 | 0 | NULL | NULL |
| 10 | 0 | NULL | NULL |

FIG.18A

| HOLDING POSITION | EXISTENCE OF SAMPLE CONTAINER | MEASURING ORDER | MEASURING STATE |
|---|---|---|---|
| 1 | NULL | NULL | NULL |
| 2 | NULL | NULL | NULL |
| 3 | NULL | NULL | NULL |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

FIG.18D

| HOLDING POSITION | EXISTENCE OF SAMPLE CONTAINER | MEASURING ORDER | MEASURING STATE |
|---|---|---|---|
| 1 | 1 | CBC+DIFF | SAMPLE LOADING (FIRST MEASUREMENT UNIT) |
| 2 | 1 | CBC+DIFF | UNMEASURED |
| 3 | NULL | NULL | NULL |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

| HOLDING POSITION (F1) | EXISTENCE OF SAMPLE CONTAINER (F2) | MEASURING ORDER (F3) | MEASURING STATE (F4) |
|---|---|---|---|
| 1 | 1 | CBC+DIFF | SAMPLE LOADING (FIRST MEASUREMENT UNIT) |
| 2 | 1 | CBC+DIFF | SAMPLE LOADING (SECOND MEASUREMENT UNIT) |
| 3 | NULL | NULL | NULL |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

| HOLDING POSITION | EXISTENCE OF SAMPLE CONTAINER | MEASURING ORDER | MEASURING STATE |
|---|---|---|---|
| 1 | 1 | CBC+DIFF | SAMPLE LOADING (FIRST MEASUREMENT UNIT) |
| 2 | 1 | CBC+DIFF | SAMPLE LOADING (SECOND MEASUREMENT UNIT) |
| 3 | 1 | CBC+DIFF | UNMEASURED |
| 4 | NULL | NULL | NULL |
| 5 | NULL | NULL | NULL |
| 6 | NULL | NULL | NULL |
| 7 | NULL | NULL | NULL |
| 8 | NULL | NULL | NULL |
| 9 | NULL | NULL | NULL |
| 10 | NULL | NULL | NULL |

FIG.18G

| HOLDING POSITION | EXISTENCE OF SAMPLE CONTAINER | MEASURING ORDER | MEASURING STATE |
|---|---|---|---|
| 1 | 1 | CBC+DIFF | SAMPLE LOADING (FIRST MEASUREMENT UNIT) |
| 2 | 1 | CBC+DIFF | SAMPLE LOADING (SECOND MEASUREMENT UNIT) |
| 3 | 1 | CBC+DIFF | UNMEASURED |
| 4 | 1 | CBC+DIFF | UNMEASURED |
| 5 | 1 | CBC+DIFF | UNMEASURED |
| 6 | 1 | CBC+DIFF | UNMEASURED |
| 7 | 1 | CBC+DIFF | UNMEASURED |
| 8 | 1 | CBC+DIFF | UNMEASURED |
| 9 | 1 | CBC+DIFF | UNMEASURED |
| 10 | 1 | CBC+DIFF | UNMEASURED |

SAMPLE PROCESSING APPARATUS AND SAMPLE PROCESSING METHOD

FIELD OF THE INVENTION

The present invention relates to a sample processing apparatus and a sample processing method, which transports a sample rack holding a plurality of sample containers, and processes the samples contained in the sample containers.

BACKGROUND

Conventionally, as a sample processing apparatus for processing samples, a multiple blood cell analyzing apparatus, a blood coagulation measuring apparatus, an immune assay analyzing apparatus, a biochemical analyzing apparatus, a urine analyzing apparatus, and a blood cell smear slide preparing apparatus have been known. Most sample processing apparatuses are configured to be provided with a transport section for transporting a sample rack holding plural sample containers, aspirates the samples from the sample containers held by the sample rack transported by the transport section, and processes the samples.

Japanese Patent Publication No. H5-072212 discloses an automatic analyzing apparatus which includes a reaction disk in which plural reaction containers are provided on a concentric circumference, and a reagent disk in which plural reagent bottles containing various reagents are provided on a concentric circle.

In the automatic analyzing apparatus, a sample dispensing probe, a reagent dispensing probe, a stirring apparatus, a cleaning apparatus, a light source, and a multi-wave-length photometer are disposed on the peripheral of the reaction disk and the reagent disk. In addition, a rack transport apparatus is provided on a rotation circumference of the sample dispensing probe and along a tangential direction of the reaction disk, and a rack number reading apparatus and a sample ID reading apparatus are disposed along a transport line of the rack transport apparatus.

The sample rack holding the sample container containing sample is transported on the transport line by the rack transport apparatus. During transport, the rack number of the sample rack is read by the rack number reading apparatus. Next, the ID number of the sample container held by the sample rack is read. Thereafter, the sample rack is transported by the rack transport apparatus until the sample container held by the sample rack reaches the position under the sample dispensing probe, and a predetermined amount of the sample in the sample container is dispensed into a reaction container by the sample dispensing probe. When the dispensing from one sample container is completed, the sample rack is transported by the rack transport apparatus such that the next sample container reaches the position under the sample dispensing probe, and the dispensing of the sample is carried out by the sample dispensing probe.

However, in the automatic analyzing apparatus disclosed in Japanese Patent Publication No. H5-072212, it is difficult to process the samples efficiently.

SUMMARY OF THE INVENTION

The scope of the present invention is defined solely by the appended claims, and is not affected to any degree by the statements within this summary.

A first aspect of the present invention is a sample processing apparatus comprising: an aspiration section for aspirating a sample from a sample container; a sample container take-out/returning section for taking out a sample container containing a sample which is to be aspirated by the aspiration section from a sample rack holding a plurality of sample containers, and for returning the sample container, from which the sample has been aspirated by the aspiration section, to the sample rack; a sample processing section for processing the sample aspirated by the aspiration section; a transport section for transporting the sample rack to a take-out position for taking out the sample container from the sample rack by the sample container take-out/returning section; and a transport controller for controlling the transport section to transport the sample rack to a processing position for performing a predetermined process on another sample container held by the sample rack when one sample container has been taken out from the sample rack by the sample container take-out/returning section.

A second aspect of the present invention is a sample processing method comprising steps of: transporting a sample rack holding a plurality of the sample containers, each sample container containing a sample, to a take-out position; taking out a sample container containing a sample which is to be aspirated from a sample rack which is positioned at the take-out position; transporting the sample rack to a processing position for performing a predetermined process on another sample container held by the sample rack when one sample container has been taken out from the sample rack; performing the predetermined process on the another sampler container; aspirating the sample from the sample container which has been taken out from the sample rack; processing the aspirated sample; transporting the sample rack to a returning position; and returning the sample container, from which the sample has been aspirated, to the sample rack which is positioned at the returning position.

BRIEF DESCRIPTION OF THE DRAWINGS

FIGS. 10A and 10B are flowcharts illustrating the flow of a sample transport controlling process carried out by a CPU of an information processing unit of a sample processing apparatus;

FIG. 11 is a schematic view illustrating the structure of a sample processing table;

FIGS. 18A to 18G are diagrams schematically illustrating an example of a state of a sample processing table.

DETAILED DESCRIPTION OF THE EMBODIMENT

In this embodiment, the sample processing apparatus is provided with a first measurement unit, a second measurement unit, a sample transport unit, and an information processing unit. The sample processing apparatus transports a sample rack holding plural sample containers by the sample transport unit, reads a sample bar-code while the sample container is taking in sample measuring of one measurement unit, or transports the sample rack by the sample transport unit for taking in or returning by the other measurement unit of the sample container.

[Configuration of Sample Processing Apparatus]

Figure 1A:
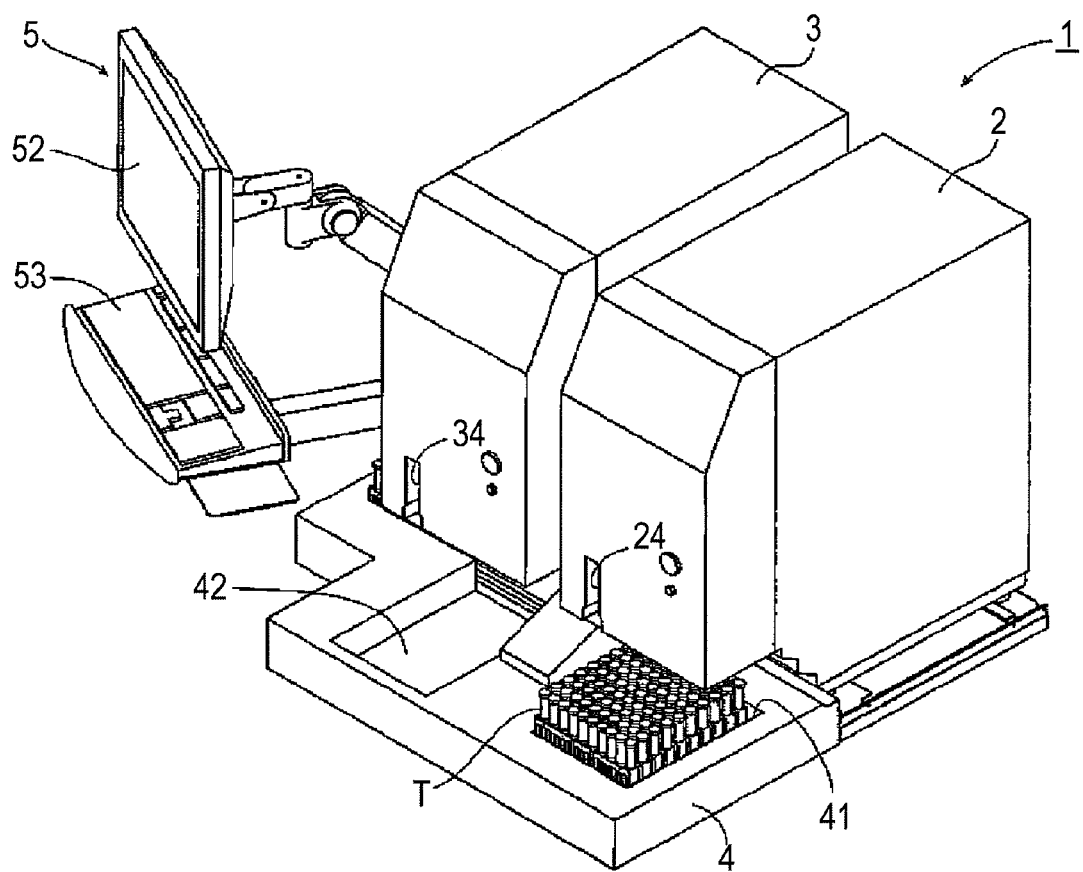
FIG. 1A is a perspective view illustrating the entire configuration of a sample processing apparatus according to an embodiment.
Figure 1B:
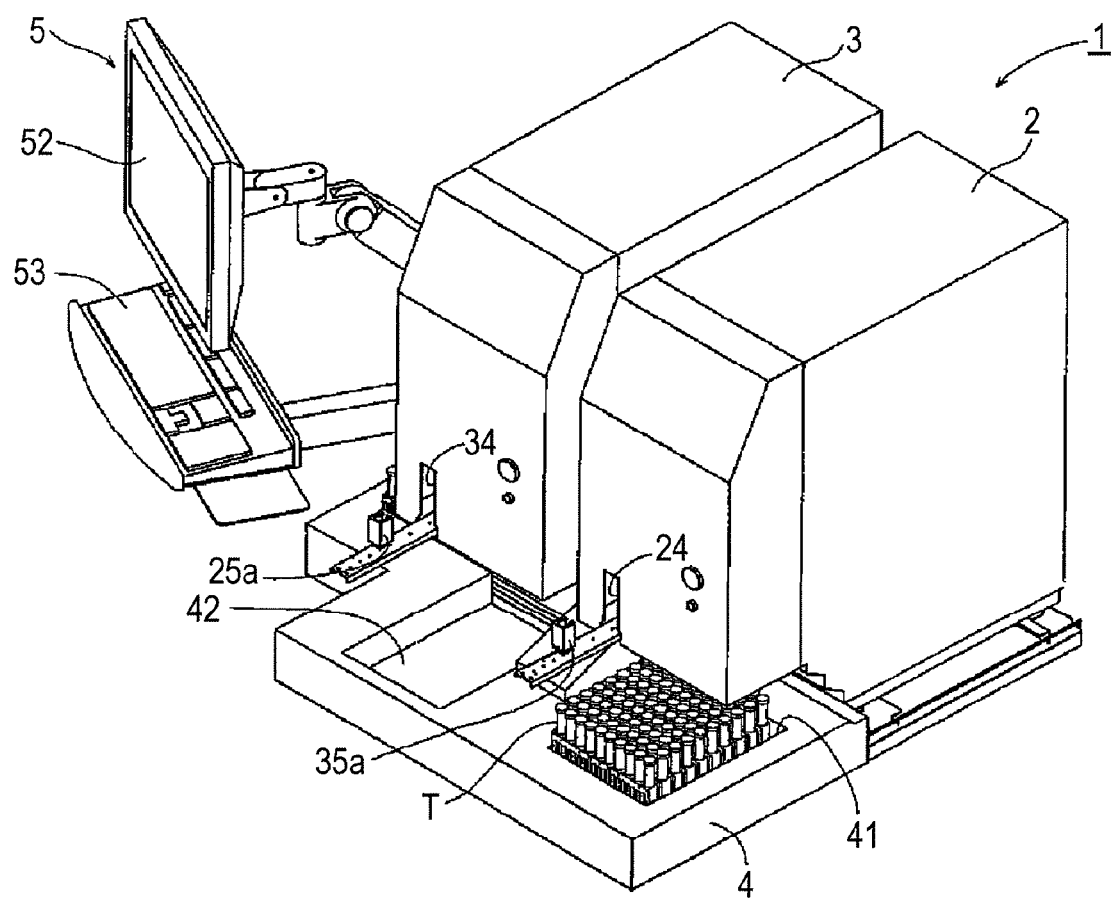
FIG. 1B is a perspective view illustrating the entire configuration of a sample processing apparatus according to an embodiment.

FIGS. 1A and 1B are perspective views illustrating the entire configuration of the sample processing apparatus according to the embodiment. The sample processing apparatus 1 according to the embodiment is a multiple blood cell analyzing apparatus which detects blood cells, such as the white blood cells, the red blood cells, and platelets which are included in a blood sample, and counts each blood cell. As shown in FIGS. 1A and 1B, the sample processing apparatus 1 is provided with a first measurement unit 2, a second measurement unit 3, a sample transport unit 4, and an information processing unit 5 which can control the first measurement unit 2, the second measurement unit 3, and the sample transport unit 4. The sample transport unit 4 is disposed on a front side surface of the first measurement unit 2 and the second measurement unit 3.

Figure 2:
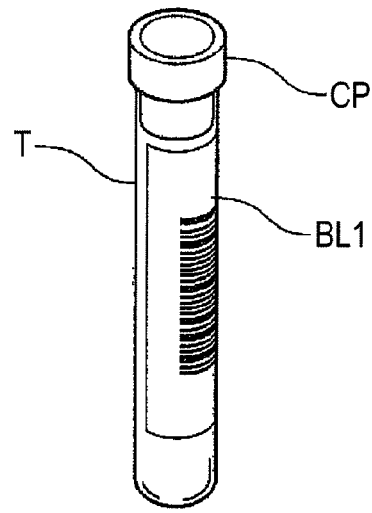
FIG. 2 is a perspective view illustrating an appearance of a sample container.

FIG. 2 is a perspective view illustrating an appearance of the sample container containing the sample. As shown in FIG. 2, the sample container T is formed in a tubular shape, and the upper end is opened. A blood sample gathered from a patient is contained in the sample container, and the opening on the upper end is sealed by a cap section CP. The sample container T is made of a transparent glass or a transparent synthetic resin, so that the blood sample therein is visible. In addition, the bar-code label BL1 is attached to the side surface of the sample container T. A bar-code indicating the sample ID is printed on the bar-code label BL1.

Figure 3:
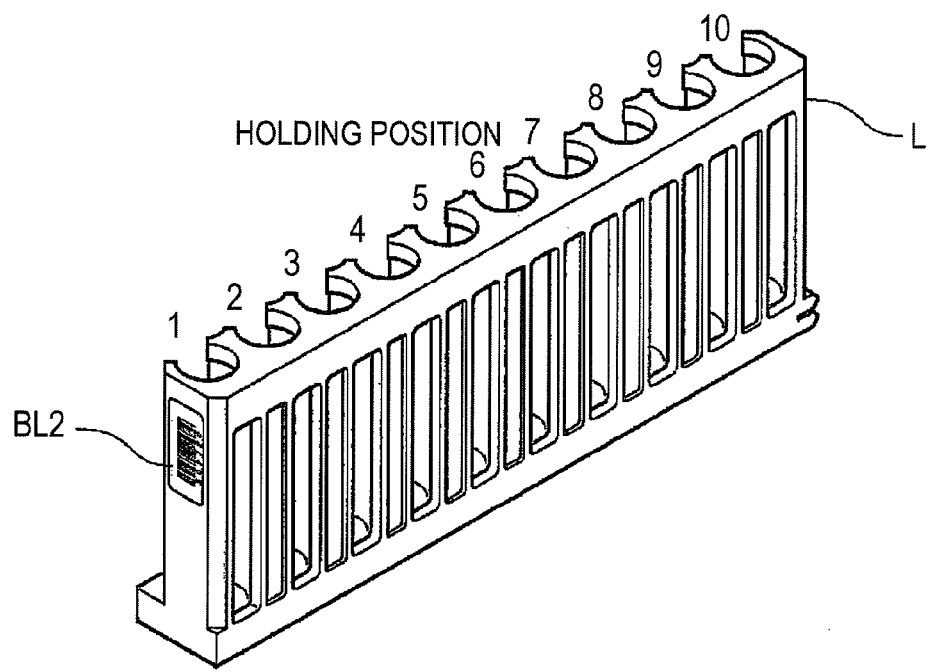
FIG. 3 is a perspective view illustrating an appearance of a sample rack.

FIG. 3 is a perspective view illustrating an appearance of the sample rack holding the plural sample containers. As shown in FIG. 3, the sample rack L can arrange and hold 10 sample containers T. Each sample container T is held in a vertical state (upright state) in the sample rack L. In addition, a bar-code label BL2 is attached on the side surface of the sample rack L. A bar-code indicating the rack ID is printed on the bar-code label BL2.

<Configuration of Measurement Unit>

Figure 4:
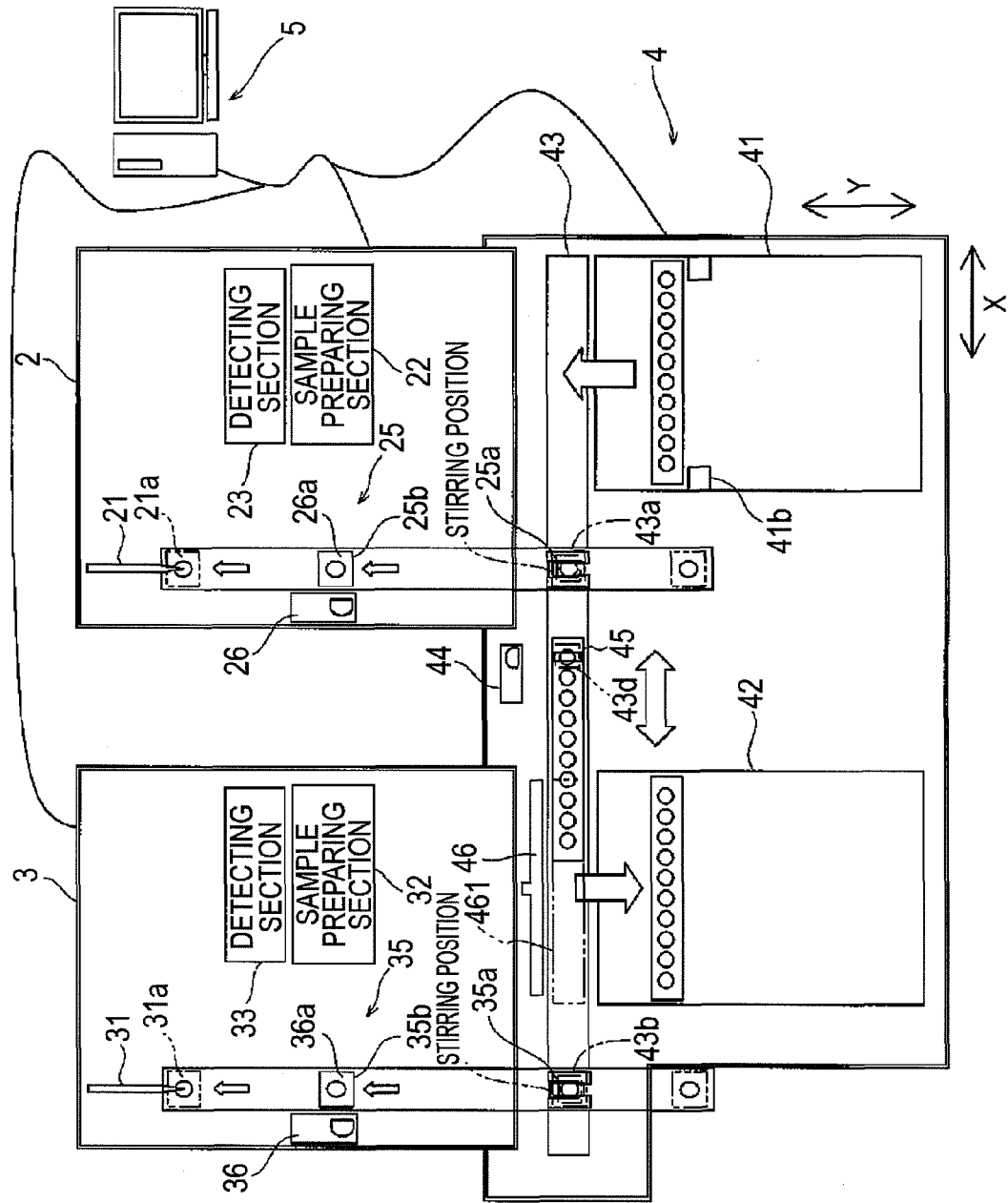
FIG. 4 is a block diagram illustrating the configuration of a measurement unit according to an embodiment.

FIG. 4 is a block diagram illustrating the configuration of the measurement unit. As shown in FIG. 4, the first measurement unit 2 is disposed on the upstream side (right side in the paper) in a transport direction (X direction) of the sample of the sample transport unit 4. The second measurement unit 3 is disposed on the downstream side (left side in the paper) in the transport direction (X direction). The first measurement unit 2 includes a sample aspirating section 21 which aspirates blood as the sample from the sample container (blood collection tube) T, a sample preparing section 22 which prepares a measuring sample to be used in measuring of blood components, such as blood cells, from the blood aspirated by the sample aspirating section 21, and a detecting section 23 which detects (measures) the blood cells from the measuring sample prepared by the sample preparing section 22. In addition, the first measurement unit 2 further includes a take-in port 24 (see FIGS. 1A and 1B) which is used to load the sample container T accommodated in the sample rack L, which is transported by a rack transport section 43 of the sample transport unit 4, into the first measurement unit 2, and a sample container transport section 25 which takes the sample container T from the sample rack L into the first measurement unit 2 and transports the sample container T up to an aspirating position by the sample aspirating section 21.

In addition, as shown in FIG. 4, an aspiration tube is provided at the tip end of the sample aspirating section 21. In addition, the sample aspirating section 21 is configured to be able to move vertically and downward, so that the aspiration tube penetrates into the cap section CP of the sample container T transported to the aspirating position so as to aspirate the blood in the sample container.

The sample preparing section 22 is provided with plural reaction chambers. In addition, the sample preparing section 22 is connected to a reagent container, and can supply a reagent, such as a staining reagent, a hemolytic agent, or a diluting fluid, to the reaction chamber. The sample preparing section 22 is also connected to the aspiration tube of the sample aspirating section 21, and can supply the blood sample aspirated by the aspiration tube to the reaction chamber. The sample preparing section 22 mixes and stirs the sample in the reaction chamber with the reagent, and prepares the sample (measuring sample) for measuring by the detecting section 23.

The detecting section 23 can detect the red blood cells (RBC) and the platelets (PLT) by using a sheath flow DC detection method. In detecting RBCs and PLTs by using the sheath flow DC detection method, a measurement sample in which a sample and a diluting fluid are mixed is measured, and measurement data obtained in this manner is analyzed and processed by the information processing unit 5 so as to obtain numerical data of the RBCs and PLTs.

In addition, the detecting section 23 is configured to detect hemoglobin (HGB) by using a SLS-hemoglobin method and detect white blood cells (WBC), neutrophils (NEUT), lymphocytes (LYMPH), eosinophils (EO), basophil (BASO) and monocytes (MONO) by using a flow cytometry method using semiconductor lasers. The detecting section 23 performs different detection methods for the WBC detection not involving detection of the five classifications of white blood cells, the detection of NEUT, LYMPH, EO, BASO, and MONO, and WBC detection involving the five classifications of white blood cells detection. In the WBC detection not involving detection of the five classifications of white blood cells, the measuring sample in which the sample, the hemolytic agent, and the diluting fluid are mixed is measured, and the information processing unit 5 analyses and processes the obtained measurement data so as to obtain the numerical data of the WBC. On the other hand, in the WBC detection involving the five classifications of white blood cells detection, the measuring sample in which the staining reagent, the hemolytic agent, and the diluting fluid for the five types of white blood cells are mixed is measured, the information processing unit 5 analyses and processes the obtained measurement data so as to obtain the numerical data of the NEUT, LYMPH, EO, BASO, MONO, and WBC.

The above-mentioned WBC, RBC, PLT, and HGB are included in a measurement item referred to as a CBC item. The WBC, RBC, PLT, HGB, NEUT, LYMPH, EO, BASO, and MONO are included in a measurement item referred to as a CBC+DIFF item. In this embodiment, the CBC+DIFF item is a measurement item which can be commonly measured in the first measurement unit 2 and the second measurement unit 3, and is a basic item which is measured on all the samples.

Figure 5:
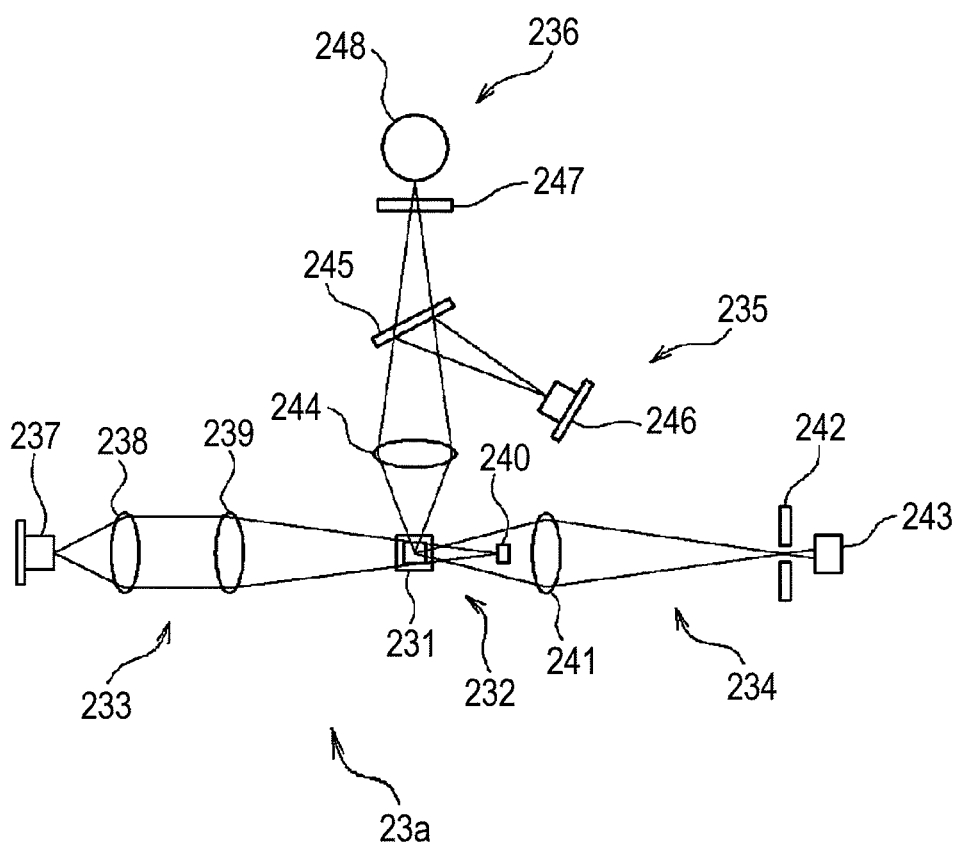
FIG. 5 is a schematic view illustrating an outline configuration of an optical detecting section for detecting WBC/DIFF.

FIG. 5 shows the outline configuration of an optical detecting section for detecting WBC/DIFF (white blood cells of five classifications) which is provided in the detecting section 23. As shown in FIG. 5, the optical detecting section 23*a* is configured to send the measuring sample into a flow cell 231, generate a liquid current in the flow cell 231, and perform measuring by irradiating the blood cells included in the liquid current passing through the flow cell 231 with a semiconductor laser light. The optical detecting section includes a sheath flow system 232, a beam spot forming system 233, a forward-scattered light receiving system 234, a side-scattered light receiving system 235, and a side-fluorescence light receiving system 236.

The sheath flow system 232 is configured such that the sample flows in the flow cell 231 in a state of being surrounded by a sheath fluid and in a state where the blood cells are aligned in a single line, so that the accuracy and reproducibility of the blood cell counting can be improved.

The beam spot forming system 233 is configured such that light irradiated from a semiconductor laser 237 passes through a collimator lens 238 and a capacitor lens 239 so as to irradiate the flow cell 231. In addition, the beam spot forming system 233 is provided with a beam stopper 240.

The forward-scattered light receiving system 234 is configured such that the forward-scattered light is condensed by a forward-condensing lens 241, and the light passing through a pin hole 242 is received by a photo diode (forward-scattered light receiving section) 243.

The side-scattered light receiving system 235 is configured such that the side-scattered light is condensed by a side-condensing lens 244, and a part of the light is reflected on a dichroic mirror 245 so as to be received by a photo diode (side-scattered light receiving section) 246.

Light scattering is a phenomenon occurring such that the particles of the blood cells act as an obstacle in terms of the traveling direction of light, and the light changes its traveling direction. By detecting the scattered light, information on the size or the material of the particles can be obtained. In particular, the information on the size of the particles (blood cells) can be obtained from the forward-scattered light. In addition, the information on the content of the particles can be obtained from the side-scattered light. When a laser light is irradiated to the blood cell particles, the side-scattered light intensity depends on the complexity of the inside of the cell (shape, size, density, or granulated amount of nucleus). Therefore, using the characteristics of the side-scattered light intensity, the measurement of the white blood cell classification and the other measurements can be carried out.

The side-fluorescence light receiving system 236 is configured such that the light which has passed through the dichroic mirror 245 further passes through a spectral filter 247 and is received by an avalanche photodiode (fluorescence light receiving system) 248.

When light is irradiated to a fluorescence material such as a stained blood cell, light is generated of which wavelength is longer than that of the irradiated light. If staining is sufficient performed, the fluorescence intensity becomes stronger. By measuring the fluorescence intensity, the information on the staining degree of the blood cells can be obtained. Therefore, by a difference of the (side) fluorescence intensity, the measurement of the white blood cell classification and the other measurements can be carried out.

Returning to FIG. 4, the configuration of the sample container transport section 25 will be described. The sample container transport section 25 is provided with a hand section 25*a* which can grasp the sample container T. The hand section 25*a* is provided with a pair of grasping members which are disposed so as to face each other. The grasping members can be moved closer to or moved away from each other. The grasping members can grasp the sample container T by being moved closer to each other in a state where the sample container T is interposed therebetween. In addition, the sample container transport section 25 can move the hand section 25*a* in a vertical direction and in a backward or forward direction (Y direction), and can also oscillate the hand section 25*a*. Thereafter, the sample container T which is contained in the sample rack L and positioned at a first sample container take-out/returning position 43*a* is grasped by the hand section 25*a*. In this state, the hand section 25*a* moves upward, so that the sample container T is pulled out of the sample rack L, and the hand section 25*a* is oscillated, so that the sample in the sample container T can be stirred.

In addition, the sample container transport section 25 is provided with a sample container setting section 25*b* which includes a hole section through which the sample container T can be inserted. The sample container T grasped by the above-mentioned hand section 25*a* moves after the stirring is completed. Then, the grasped sample container T is inserted into the hole section of the sample container setting section 25*b*. Thereafter, the grasping members are moved away from each other, so that the sample container T is released from the hand section 25*a*, and the sample container T is set in the sample container setting section 25*b*. The sample container setting section 25*b* can horizontally move in the Y direction by a driving force of the stepping motor.

In the first measurement unit 2, a bar-code reading section 26 is provided. The sample container setting section 25*b* can move to a bar-code reading position 26*a* near the bar-code reading section 26 and a aspirating position 21*a* at which aspiration is carried out by the sample aspirating section 21. When the sample container setting section 25*b* moves to the bar-code reading position 26*a*, the set sample container T is horizontally rotated by a rotation mechanism and the sample bar-code is read by the bar-code reading section 26. Accordingly, even when the bar-code label BL1 of the sample container T is positioned on the opposite side with respect to the bar-code reading section 26, the bar-code label BL1 can face the bar-code reading section 26 by rotating the sample container T and the bar-code reading section 26 can read the sample bar-code. In addition, when the sample container setting section 25*b* is moved to the aspirating position, the sample is aspirated from the set sample container T by the sample aspirating section 21.

Next, the configuration of the second measurement unit 3 will be described. The configuration of the second measurement unit 3 is the same as that of the first measurement unit 2. The second measurement unit 3 includes a sample aspirating section 31, a sample preparing section 32 which prepares a measuring sample to be used in measuring of the blood components, such as blood cells, from the blood aspirated by the sample aspirating section 31, and a detecting section 33 which detects the blood cells from the measuring sample prepared by the sample preparing section 32. In addition, the second measurement unit 3 further includes a take-in port 34 (see FIGS. 1A and 1B) which is used to take in the sample container T accommodated in the sample rack L, which is transported by the rack transport section 43 of the sample transport unit 4, into the second measurement unit 3, and a sample container transport section 35 which loads the sample container T from the sample rack L into the second measurement unit 3 and transports the sample container T up to an aspirating position by the sample aspirating section 31. The configurations of the sample aspirating section 31, the sample preparing section 32, the detecting section 33, the take-in port 34, the sample container transport section 35, and the bar-code reading section 36 are the same as those of the sample aspirating section 21, the sample preparing section 22, the detecting section 23, the take-in port 24, and the sample container transport section 25, so that the descriptions thereof will be omitted.

Similarly to the first measurement unit 2, the second measurement unit 3 can perform the measurement of the sample regarding each of the measurement items, such as WBC which is the above-mentioned CBC+DIFF item, RBC, PLT, HGB, NEUT, LYMPH, EO, BASO, and MONO. The configuration of the second measurement unit 3 is the same as that of the first measurement unit, so that the description thereof will be omitted.

The first measurement unit 2 and the second measurement unit 3 can take in the sample container T containing another sample while a measuring sample prepared from one sample is measured by the detecting sections 23 and 33.

<Configuration of Sample Transport Unit>

Next, the configuration of the sample transport unit 4 will be described. As shown in FIGS. 1A and 1B, the sample transport unit 4 is disposed in front of the first measurement unit 2 and the second measurement unit 3 of the sample processing apparatus 1. The sample transport unit 4 can transport the sample rack L in order to supply the sample to the first measurement unit 2 and the second measurement unit 3.

Figure 6:
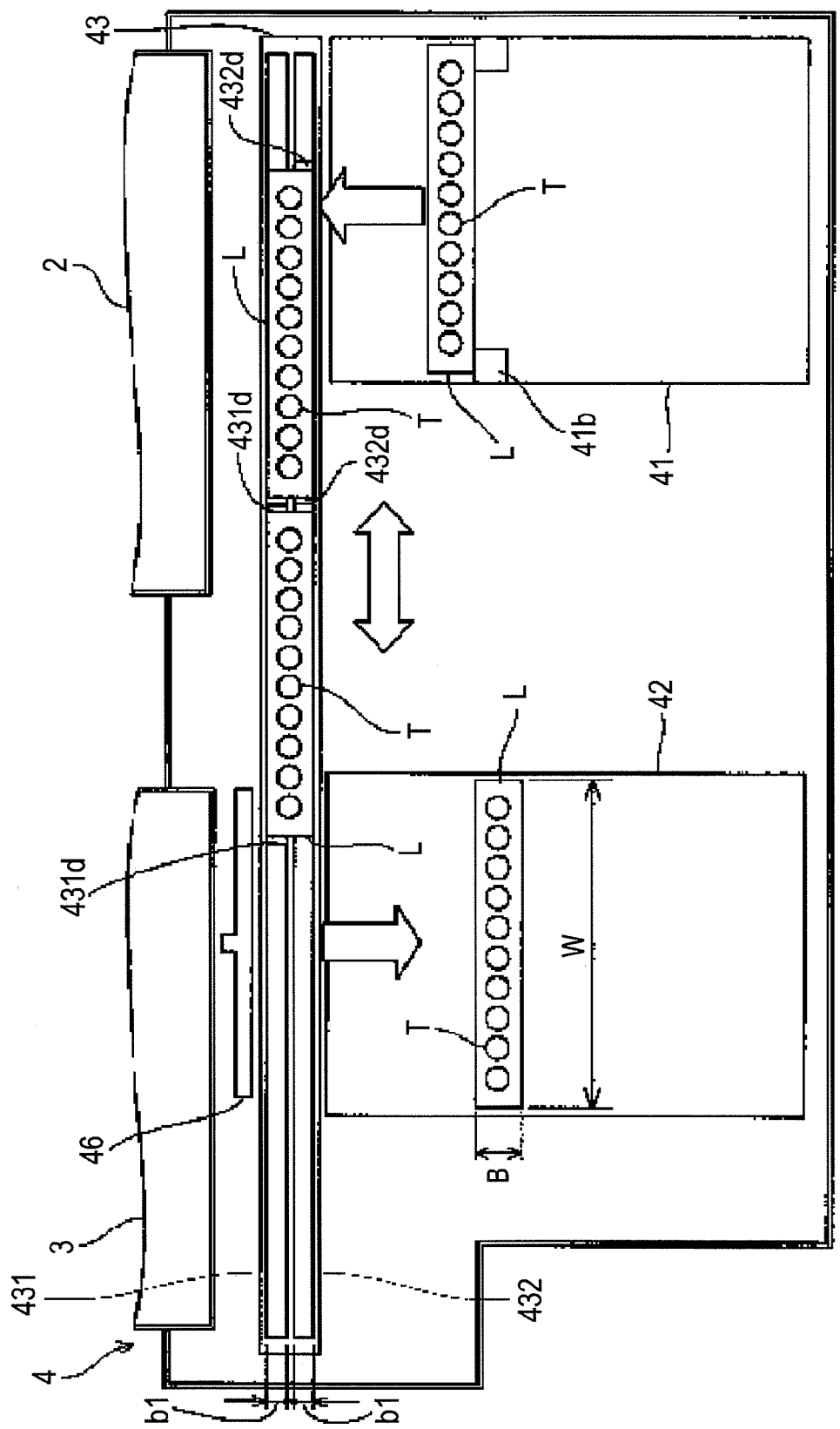
FIG. 6 is a plan view illustrating the configuration of a sample transport unit.

FIG. 6 is a plan view illustrating the configuration of the sample transport unit 4. As shown in FIG. 6, the sample transport unit 4 is provided with a before-analysis rack holding section 41, an after-analysis rack holding section 42, the rack transport section 43, a bar-code reading section 44, and a sample container sensor 45 (see FIG. 4) which detects the existence of the sample container T. The before-analysis rack holding section 41 can temporarily hold the plural sample racks L which hold the sample containers T which have yet to be subjected to the analysis. The after-analysis rack holding section 42 can temporarily hold the plural sample racks L which hold the sample container T in which the sample has been aspirated by the first measurement unit 2 and the second measurement unit 3. The rack transport section 43 horizontally moves the sample rack L in a straight line in the arrow direction X in order to supply the sample to the first measurement unit 2 or the second measurement unit 3. Then, the rack transport section transports the sample rack L received from the before-analysis rack holding section 41 to the after-analysis rack holding section 42.

The before-analysis rack holding section 41 has a quadrangular shape in plan view, and its width is slightly larger than the width of the sample rack L. The before-analysis rack holding section 41 is formed to be lower by one stage than the surrounding surface, and on an upper face thereof, the before-analysis sample racks L are held. In addition, rack sending sections 41*b* are provided in both faces of the before-analysis rack holding section 41 so as to protrude inward. The rack sending sections 41*b* protrude, and thus the sample rack L comes into contact with the rack sending sections 41*b*. In this state, the rack sending sections are moved backward (a direction so as to be closer to the rack transport section 43) and thus the sample rack L is moved backward. The rack sending sections 41*b* are configured to be driven by a stepping motor which is provided below the before-analysis rack holding section 41.

As shown in FIG. 6, the rack transport section 43 can move the sample rack L sent by the before-analysis rack holding section 41 in the X direction as described above.

Returning to FIG. 4, on the transport path of the sample rack L by the rack transport section 43, there are the first sample container take-out/returning position 43*a* at which the sample container containing the sample as an aspiration subject of the first measurement unit 2 is taken out from the sample rack L, and second sample container take-out/returning position 43*b* at which the sample container containing the sample as an aspiration subject of the second measurement unit 3 is taken out from the sample rack L. When the sample transport unit 4 is controlled by the information processing unit 5 so as to transport the sample to the first sample container take-out/returning position 43*a* or the second sample container take-out/returning position 43*b*, the hand section 25*a* or a hand section 35*a* of the corresponding measurement unit grasps the transported sample container T and takes out the sample container T from the sample rack L so as to supply the sample to the first measurement unit 2 or the second measurement unit 3. As a result, the hand section 25*a* or 35*a* grasping the sample container T enters into the housing of the first measurement unit 2 or the second measurement unit 3 as described above, and thereby the sample is taken into the first measurement unit 2 or the second measurement unit 3. The rack transport section 43 can transport the sample rack L also while the sample is being taken in the first measurement unit 2 or the second measurement unit 3. Therefore, since another sample cannot be taken into the measurement unit while one of the first measurement unit 2 and the second measurement unit 3 is being taken in with the sample, the sample rack L can be transported to the other measurement unit so as to take in the sample.

Here, the configuration of the rack transport section 43 will be described in detail with reference to FIGS. 6 to 8. As shown in FIG. 6, the rack transport section 43 has two independently operable belts, that is, a first belt 431 and a second belt 432. Width b1 in a direction of the arrow Y of the first belt 431 and the second belt 432 is equal to or greater than half of a width B in the direction of the arrow Y of the sample rack L. The first belt 431 and the second belt 432 are disposed in parallel so as not to protrude from the width B of the sample rack L when the rack transport section 43 transports the sample rack L.

Figure 7:
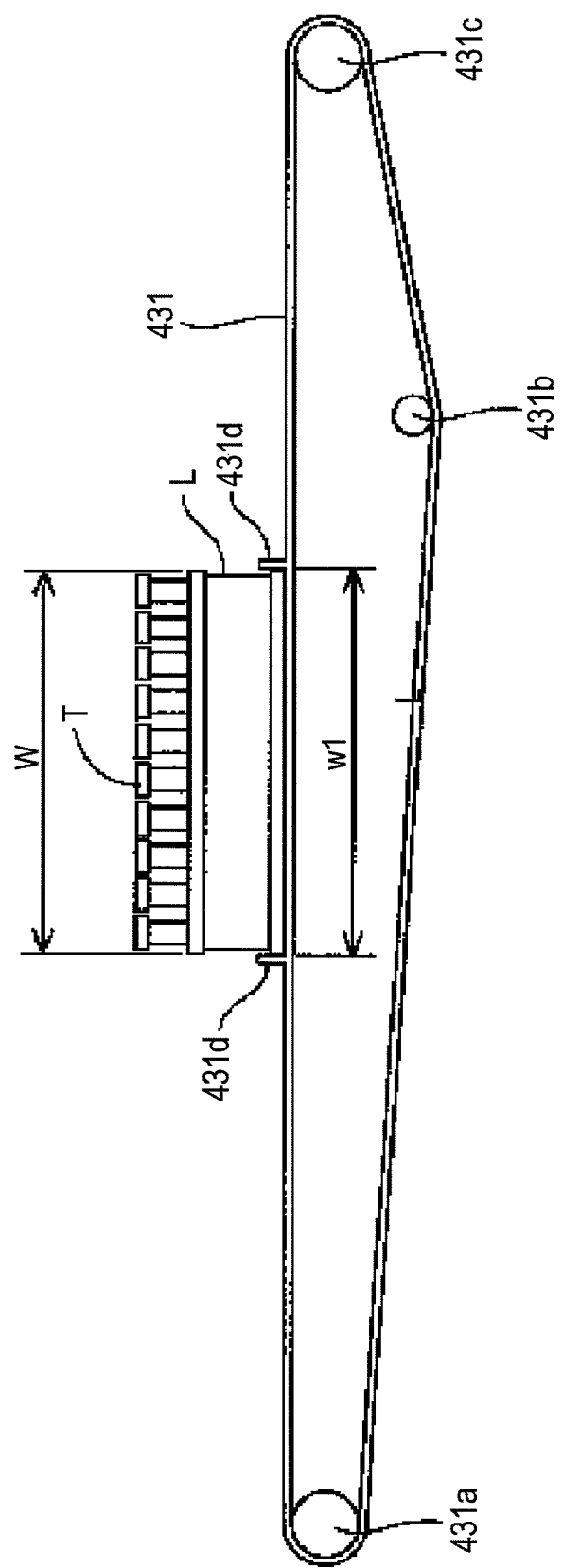
FIG. 7 is a front view illustrating the configuration of a first belt of a sample transport unit.
Figure 8:
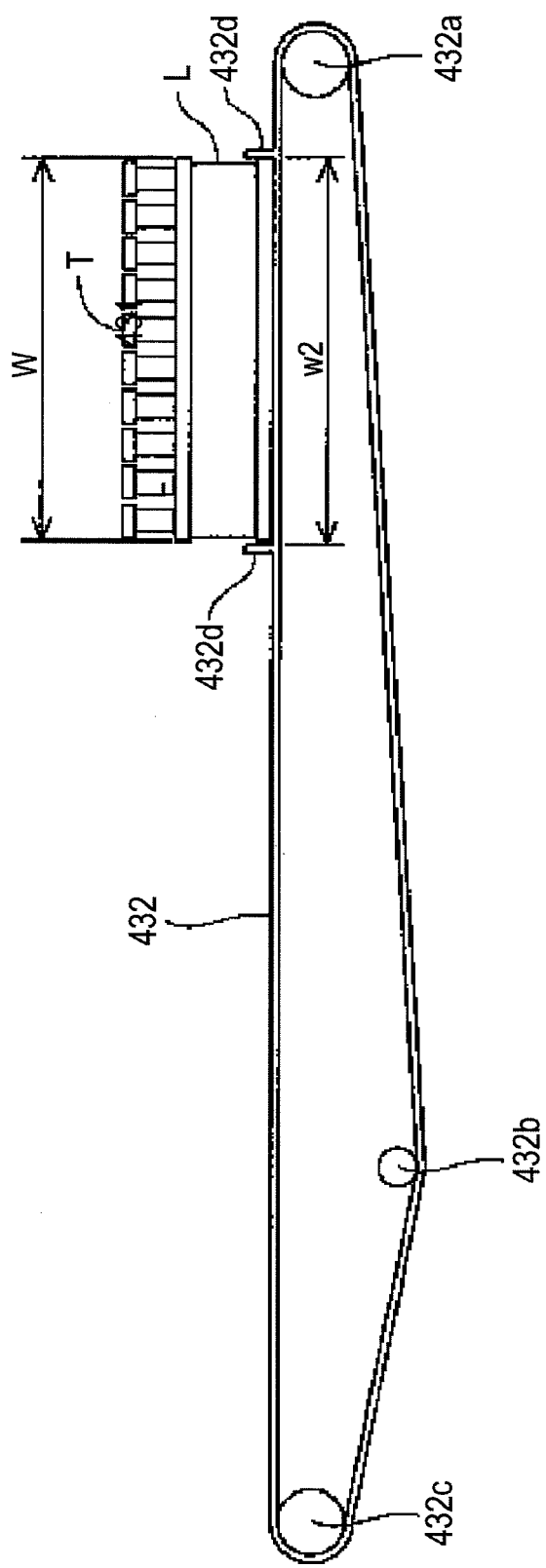
FIG. 8 is a front view illustrating the configuration of a second belt of a sample transport unit.

FIG. 7 is a front view illustrating the configuration of the first belt 431, and FIG. 8 is a front view illustrating the configuration of the second belt 432. As shown in FIGS. 7 and 8, the first belt 431 and the second belt 432 are annularly formed. The first belt 431 is disposed so as to surround rollers 431*a* to 431*c* and the second belt 432 is disposed so as to surround rollers 432*a* to 432*c*. In the outer peripheral section of the first belt 431, two protrusions 431*d* are provided so as to have an inner width w1 slightly larger (for example, 1 mm) than a width W in the X direction of the sample rack L, and similarly as shown in FIG. 8, in the outer peripheral section of the second belt 432, two protrusions 432d are provided so as to have the substantially same inner width w2 as the inner width w1. The first belt 431 is configured such that the sample rack L held inside of the two protrusions 431d is moved in the direction of the arrow X by being moved along the outer peripheries of the rollers 431a to 431c by a stepping motor. The second belt 432 is configured such that the sample rack L held inside of the two protrusions 432d is moved in the direction of the arrow X by being moved along the outer peripheries of the rollers 432a to 432c by a stepping motor. In addition, the first belt 431 and the second belt 432 are configured so as to move the sample rack L independently of each other. Therefore, the rack transport section 43 can transport the sample rack L such that the sample is transported up to the first sample container take-out/returning position 43a, the second sample container take-out/returning position 43b, and a reading position 43d for reading the bar-code printed on the bar-code label BL1 of the sample container T by the bar-code reading section 44.

Returning to FIG. 4, the bar-code reading section 44 is configured to read the bar-code printed on the bar-code label BL1 of the sample container T shown in FIG. 5, and to read the bar-code printed on the bar-code label BL2 which is attached to the sample rack L. In addition, the bar-code reading section 44 is configured to read the bar-code of the sample container T while the sample container T of the subject accommodated in the sample rack L is being rotated in the horizontal direction by a rotation apparatus. Therefore, even when the bar-code of the sample container T is attached to an opposite side with respect to the bar-code reading section 44, by rotating the sample container T, the bar-code can face the bar-code reading section 44. In addition, the bar-code printed on the bar-code label BL2 of the sample rack L is uniquely assigned to each rack and used to manage the analysis result of the sample.

The sample container sensor 45 is a contact sensor and has a contact piece, a light-emitting element for emitting light, and a light-receiving element. The sample container sensor 45 is configured such that the contact piece is bent when brought into contact with a substance to be detected which is a detection object and the light emitted from the light-emitting element is thus reflected by the contact piece and enters the light-receiving element. Accordingly, while the sample container T which is a detection object accommodated in the sample rack L passes under the sample container sensor 45, the contact piece is bent by the sample container T and the sample container T can be detected. The sample container sensor 45 is provided at the bar-code reading position 43d. Therefore, the existence of the sample container T at the bar-code reading position 43d can be detected by the sample container sensor 45.

At the downstream end of the rack transport section 43 in the transport direction, the after-analysis rack holding section 42 to be described later is provided. A rack delivery section 46 is provided in the rear side of the after-analysis rack holding section 42. The rack delivery section 46 is configured to horizontally move in a straight line in the direction of the arrow Y by a driving force of the stepping motor. Therefore, when the sample rack L is transported to a position 461 (hereinafter, referred to as "after-analysis rack delivery position") between the after-analysis rack holding section 42 and the rack delivery section 46, the sample rack L can be moved into the after-analysis rack holding section 42 by moving the rack delivery section 46 toward the after-analysis rack holding section 42.

The after-analysis rack holding section 42 has a quadrangular shape in plan view, and its width is slightly larger than the width of the sample rack L. The after-analysis rack holding section 42 is formed to be lower by one stage than the surrounding surface, and on an upper face thereof, the analyzed sample racks L are held. The after-analysis rack holding section 42 is connected to the above-mentioned rack transport section 43 and, as described above, sends the sample rack L from the rack transport section 43 by the rack delivery section 46.

According to the configuration as described above, the sample transport unit 4 moves the sample rack L held on the before-analysis rack holding section 41 to the rack transport section 43, and the sample rack is further transported by the rack transport section 43 so that the sample can be supplied to the first measurement unit 2 or the second measurement unit 3. In addition, the sample rack L accommodating the samples which are completely aspirated is moved to the after-analysis rack delivery position 461 by the rack transport section 43, and delivered to the after-analysis rack holding section 42 by the rack delivery section 46. When the plural sample racks L are held on the before-analysis rack holding section 41, the sample racks L accommodating the samples which are completely analyzed are sequentially delivered to the after-analysis rack holding section 42 by the rack delivery section 46. The plural sample racks L are stored in the after-analysis rack holding section 42.

<Configuration of Information Processing Unit>

Figure 9:
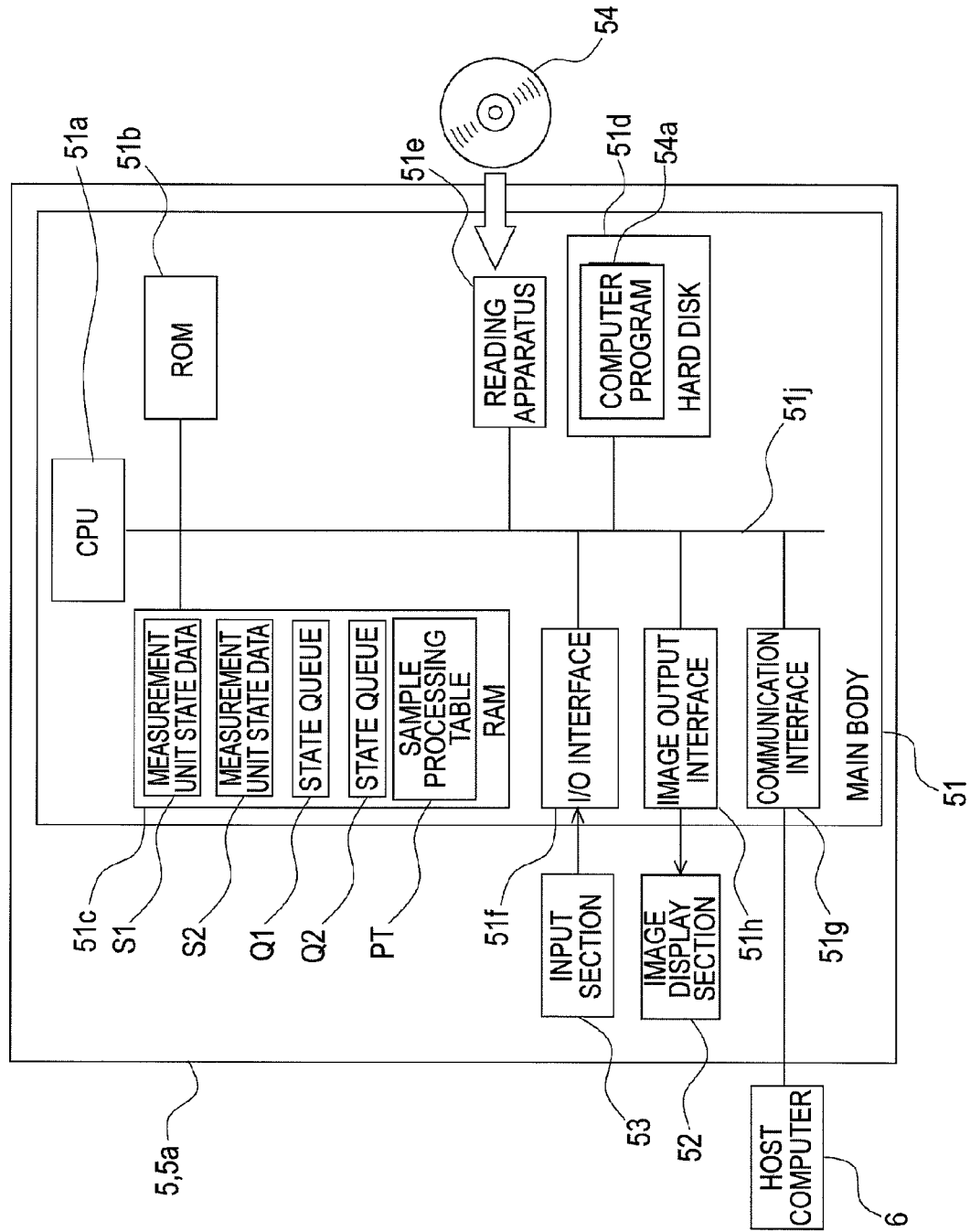
FIG. 9 is a block diagram illustrating the configuration of an information processing unit according to an embodiment.

Next, the configuration of the information processing unit 5 will be described. The information processing unit 5 is composed of a computer. FIG. 9 is a block diagram illustrating the configuration of the information processing unit 5. The information processing unit 5 is realized by a computer 5a. As shown in FIG. 9, the computer 5a includes a main body 51, an image display section 52 and an input section 53. The main body 51 includes a CPU 51a, a ROM 51b, a RAM 51c, a hard disk 51d, a reading device 51e, an I/O interface 51f, a communication interface 51g and an image output interface 51h. The CPU 51a, ROM 51b, RAM 51c, hard disk 51d, reading device 51e, I/O interface 51f, communication interface 51g and image output interface 51h are connected to each other by a bus 51j.

The CPU 51a can execute a computer program loaded to the RAM 51c. The CPU 51a executes a computer program 54a for analyzing a sample and controlling the first measurement unit 2, the second measurement unit 3, and the sample transport unit 4, which will be described later, so that the computer 5a functions as the information processing unit 5.

The ROM 51b is composed of a mask ROM, a PROM, an EPROM, an EEPROM or the like and the computer program executed by the CPU 51a and data used for the computer program are recorded in the ROM.

The RAM 51c is composed of a SRAM, a DRAM or the like. The RAM 51c is used to read the computer program 54a recorded in the hard disk 51d. In addition, the RAM is used as an operating area of the CPU 51a when the CPU 51a executes a computer program.

In the RAM 51c, measurement unit state data areas S1 and S2 showing the states of the first measurement unit 2 and the second measurement unit 3 are provided. In the measurement unit state data areas S1 and S2, any one of "Sample Take-in Possible", "Sample Take-in/Returning Impossible", and "Sample Returning Possible" is stored as data. Here, when the measurement unit is in a standby state of standing by to take in the sample instead of carrying out the take-in and measuring of the sample, the state of the measurement unit becomes "Sample Take-in Possible". In addition, when the measurement unit carries out the taking in the sample, the state of the measurement unit becomes "Sample Take-in/Returning Impossible". Furthermore, when the measurement unit ends the aspirating the sample and is in the state of standing by to return the sample to the sample rack L of the sample container T, the state of the measurement unit becomes "Sample Returning Possible". After the measurement unit measures the measuring sample by the detecting sections 23 and 33 (that is, detecting the blood cell) and the returning of the sample container T is completed, the state of the measurement unit becomes "Sample Take-in Possible" in which a new sample can be taken in.

In addition, in the RAM 51c, areas of state queues Q1 and Q2 in which the state data of the first measurement unit 2 and the second measurement unit 3 is stored are provided. The state queues Q1 and Q2 receive the state data of the first measurement unit 2 and the second measurement unit 3 in real time, and store the state data in a FIFO list structure.

In the hard disk 51d, various computer programs for execution by the CPU 51a, such as an operating system and an application program, and data which is used to execute the computer programs, are installed. The computer program 54a to be described later is also installed in the hard disk 51d.

The reading device 51e is composed of a flexible disk drive, a CD-ROM drive, a DVD-ROM drive or the like and can read the computer program or data recorded in a portable recording medium 54. In the portable recording medium 54, the computer program 54a for prompting the computer to function as the information processing unit 5 is stored. The computer 5a can read the computer program 54a from the portable recording medium 54 and install the computer program 54a in the hard disk 51d.

The computer program 54a is provided by the portable recording medium 54 and can be also provided from an external device, which is connected to the computer 5a by an electric communication line (which may be wired or wireless) to communicate therewith, through the electric communication line. For example, the computer program 54a is stored in a hard disk of a server computer on the internet and the computer 5a accesses the server computer to download the computer program and install the computer program in the hard disk 51d.

Furthermore, in the hard disk 51d, for example, a multi-tasking operating system such as Windows (registered trade name), which is made and distributed by Microsoft corporation in America, is installed. In the following description, the computer program 54a according to this embodiment operates on the above operating system.

The I/O interface 51f is composed of, for example, a serial interface such as USB, IEEE1394 or RS-232C, a parallel interface such as SCSI, IDE or IEEE1284, and an analog interface including a D/A converter and an A/D converter. The input section 53 composed of a keyboard and a mouse is connected to the I/O interface 51f and the user uses the input section 53 so as to input data to the computer 5a. In addition, the I/O interface 51f is connected to the first measurement unit 2, the second measurement unit 3, and the sample transport unit 4. Therefore, the information processing unit 5 can control the first measurement unit 2, the second measurement unit 3, and the sample transport unit 4.

The communication interface 51g is an Ethernet (registered trade name) interface. The communication interface 51g is connected to a host computer 6 via a LAN. Via the communication interface 51g, the computer 5a can send and receive data to and from the host computer 6 connected to the LAN by using a predetermined communication protocol.

The image output interface 51h is connected to the image display section 52 composed of a LCD or a CRT so as to output a picture signal corresponding to the image data provided from the CPU 51a to the image display section 52. The image display section 52 displays an image (screen) in accordance with an input picture signal.

[Operation of Sample Processing Apparatus 1]

Hereinafter, the operation of the sample processing apparatus 1 according to this embodiment will be described.

<Sample Transport Controlling Process>

Figure 10A:
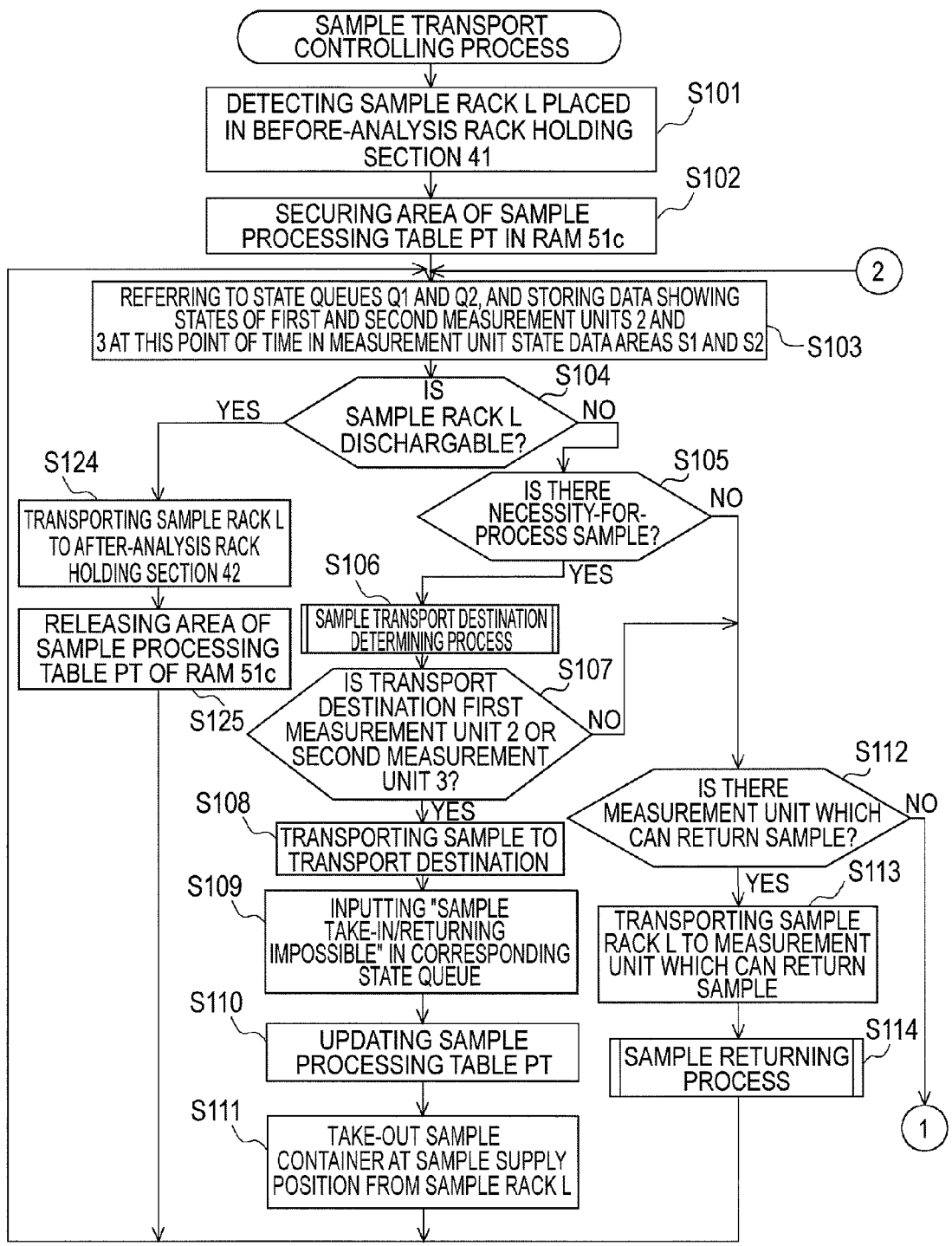

FIGS. 10A and 10B are flowcharts illustrating the flow of the sample transport controlling process carried out by the information processing unit 5 of the sample processing apparatus 1. An operator places the sample rack L accommodating the plural sample containers T, which contain samples, on the before-analysis rack holding section 41. In this state, the operator operates the input section 53 so as to instruct the information processing unit 5 to perform the sample measuring. The CPU 51a of the information processing unit 5 receives the instruction of performing the sample measuring, and then performs the following sample transport controlling process. First, when detecting the sample rack L which is held on the before-analysis rack holding section 41 by a sensor (Step S101), the CPU 51a secures an area for sample processing table which is used to measure the sample by the RAM 51c (Step S102).

FIG. 11 is a schematic view illustrating the structure of the sample processing table. A sample processing table PT is a table for securing each piece of the information on, such as, the holding position of each sample in the sample rack L, the existence of the sample container, the measuring order, and the measuring state of the sample, for each sample rack L. As shown in FIG. 11, the sample processing table PT is composed of 10 rows, and each row corresponds to the sample which is accommodated to the sample rack L. A field (column) F1 of the holding position of the sample rack L, a field F2 of the existence of the sample, a field F3 of the measuring order, and a field F4 of the measuring state are provided in the sample processing table PT. In the field F1, information of "1" to "10" showing the holding positions of the sample in the sample rack L is stored. In the field F2, when there is the sample container T at the corresponding holding position, "1" is stored, and when there is no sample container T at the corresponding holding position, "0" is stored. In the field F3, information of the measurement item showing the measuring order is stored. Further, as described above, since the CBC+DIFF item includes each item of WBC, RBC, PLT, HGB, NEUT, LYMPH, EO, BASO, and MONO, the respective pieces of the information of the measurement items may be individually stored in the field F3 and, as shown in FIG. 11, the information representing the "CBC+DIFF" may be stored in the field F3. In the field F4, any one of four type information, that is, "Unmeasured", "Take-in Sample (first measurement unit)", "Take-in Sample (second measurement unit)", and "Measured" is stored as information indicating measuring state. In Step S102, all the respective cells are in a state of being filled with a blank (NULL is stored) excepting the field F1 of the sample processing table PT. In addition, when two sample processing tables PT exist, all the samples of the sample rack L corresponding to one sample processing table PT is processed, and the following processes are carried out on the one sample processing table PT as a subject until the samples are transported to the after-analysis rack holding section 42, and then the following processes are carried out on the other sample processing table PT.

Returning FIG. 10A, the CPU 51a refers to the state queues Q1 and Q2 so as to store the data showing the state of the first measurement unit 2 and the second measurement unit 3 at this point of time in the measurement unit state data areas S1 and S2 (Step S103). Here, in the state queues Q1 and Q2, the plural state data may be stored. In this case, the CPU 51a sequentially reads out the state data from the state queues Q1 and Q2, and stores the finally-read data in the measurement unit state data areas S1 and S2. The data which is finally read from the state queues Q1 and Q2 shows the final state of the first measurement unit 2 and the second measurement unit 3, that is, the state of the first measurement unit 2 and the second measurement unit 3 at this point of time. Further, initial values of the state queues Q1 and Q2 are "Sample Take-in Possible".

Next, the CPU 51a determines whether or not the sample rack L can be discharged (Step S104). In this process, the CPU 51a refers to the sample processing table PT so as to store any one of "0" and "1" to the field F2 with respect to all the holding positions (that is, there is no cell filled with "NULL"). In addition, when "Measured" is stored in the field F4 in all the records in which "1" is stored in the field F2, there is no sample container T which is necessary to be subjected to the process in the sample container T accommodated to the sample rack L so that the sample rack L can be discharged. On the other hand, when "NULL" is stored in the field F2 with respect to at least one of the holding positions, or when "Unmeasured" or "Sample Take-in" is stored in the field F4, since there is a sample container T which is necessary to be subjected to the process in the sample rack L, the sample rack L cannot be discharged.

In Step S104, when the sample rack L cannot be discharged (NO in Step S104), the CPU 51a determines whether or not there is a necessity-for-process sample with reference to the sample processing table PT (Step S105). The "Necessity-For-Process Sample" indicates a sample which is confirmed of the measuring order and is not measured. That is, in the sample processing table PT, a sample in which the information of the measuring order is stored in the field F3 and the information of the "Unmeasured" is stored in the field F4 corresponds to the "Necessity-For-Process Sample".

In Step S105 described above, when there is a necessity-for-process sample (YES in Step S105), the CPU 51a performs a sample transport destination determining process (Step S106).

Figure 12:
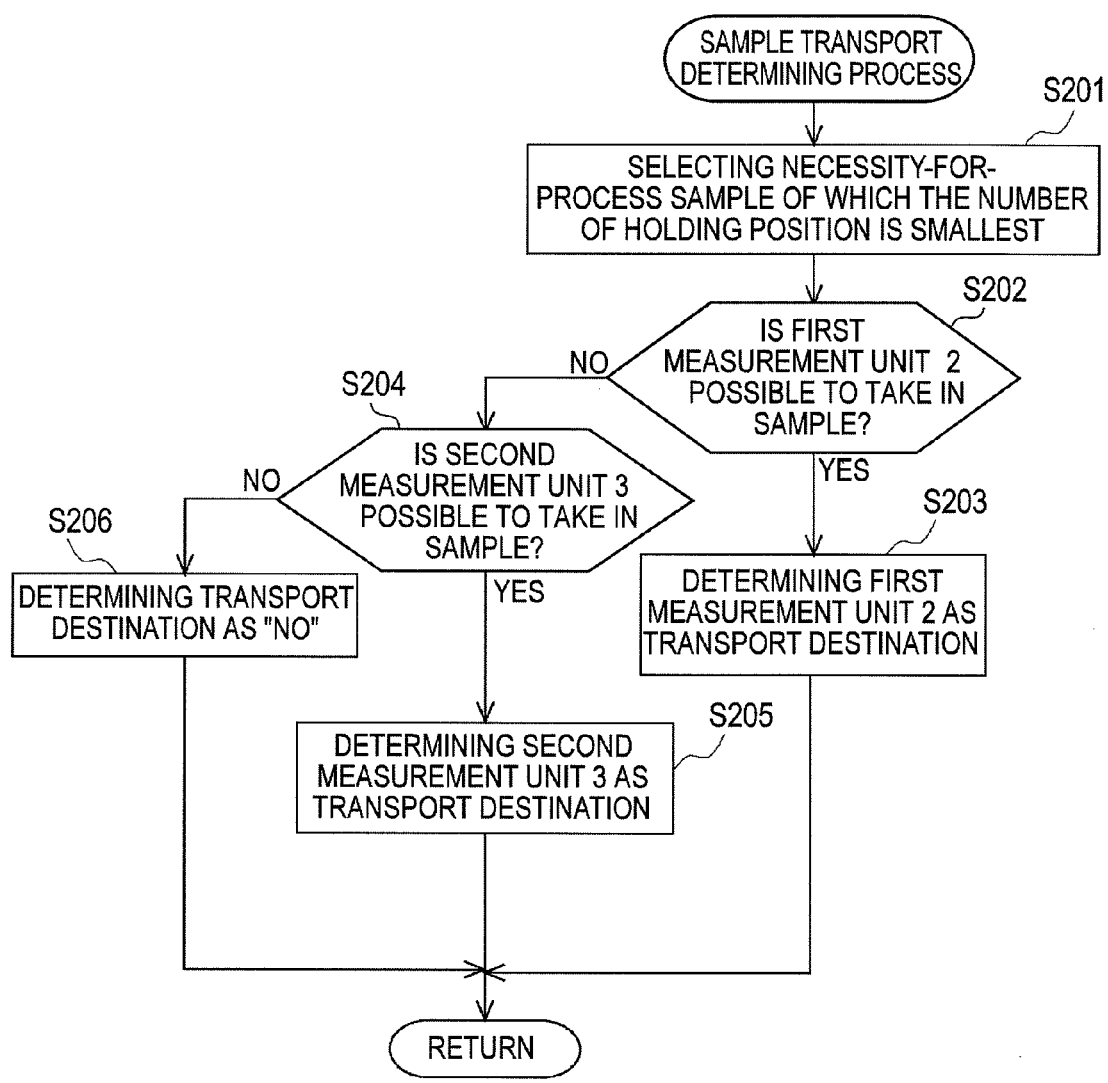
FIG. 12 is a flowchart illustrating the procedure of a sample transport destination determining process carried out by a CPU of an information processing unit of a sample processing apparatus.

FIG. 12 is a flowchart illustrating the procedure of the sample transport destination determining process. In the sample transport destination determining process, the CPU 51a first refers to the sample processing table PT so as to select a necessity-for-process sample of which the holding position number is minimized (Step S201). Next, the CPU 51a refers to the measurement unit state data area S1 of the RAM 51c so as to determine whether or not the state of the first measurement unit 2 is "Sample Take-in Possible" (Step S202). In Step S202, when the state of the first measurement unit 2 is "Sample Take-in Possible" (YES in Step S202), the CPU 51a determines the first measurement unit 2 to the transport destination (Step S203), and returns the process to an invoked address of the sample transport destination determining process.

On the other hand, in Step S202, when the state of the first measurement unit 2 is "Sample Take-in/Returning Impossible" or "Sample Returning Possible" (NO in Step S202), the CPU 51a refers to the measurement unit state data area S2 of the RAM 51c so as to determine whether or not the state of the second measurement unit 3 is "Sample Take-in Possible" (Step S204). In Step S204, when the state of the second measurement unit 3 is "Sample Take-in Possible" (YES in Step S204), the CPU 51a determines the second measurement unit 3 to the transport destination (Step S205), and returns the process to an invoked address of the sample transport destination determining process.

In Step S204, when the state of the second measurement unit 3 is "Sample Take-in/Returning Impossible" or "Sample Returning Possible" (NO in Step S204), the CPU 51a determines the transport destination as "NO" (Step S206), and returns the process to an invoked address of the sample transport destination determining process.

Returning to FIG. 10A, the CPU 51a determines whether the determined transport destination is the first measurement unit 2 or the second measurement unit 3 (Step S107). When the determined transport destination is the first measurement unit 2 or the second measurement unit 3 (YES in Step S107), the CPU transports the sample selected in the sample transport destination determining process to the transport destination (Step S108). Further, in this process, when the transport destination is the first measurement unit 2, the CPU 51a controls the sample transport unit 4 to position the selected sample at the first sample container—take-out/returning position 43a. When the transport destination is the second measurement unit 3, the CPU controls the sample transport unit 4 to position the selected sample at the second sample container takeout/returning position 43b.

Next, the CPU 51a inputs "Sample Take-in/Returning Impossible" to the state queue corresponding to the measurement unit of the transport destination (Step S109). In addition, the CPU 51a changes the measuring state in the sample processing table PT of the sample to "Sample Take-in (first measurement unit)" in order to except the sample from the necessity-for-process sample, so that the sample process table PT is updated (Step S110).

Furthermore, the CPU 51a controls the sample container transport section of the measurement unit of the transport destination and pulls out the sample container T positioned at the sample container take-out/returning position from the sample rack L (Step S111).

Thereafter, the CPU 51a performs a sample take-in process and a sample measuring process to be described later. Therefore, the selected sample container T is taken in the first measurement unit 2 or the second measurement unit 3, and the sample is aspirated from the sample container T. Since the sample take-in process takes tens of seconds, after the process of Step S111 described above is completed, the CPU 51a returns the process to Step S103, and performs the subsequent processes of Step S103 in parallel to the sample take-in process.

In Step S105, when there is no necessity-for-process sample (NO in Step S105), or when the transport destination determined by the sample transport destination determining process in Step S107 is "NO" (NO in Step S107), the CPU 51a refers to the measurement unit state data areas S1 and S2 so as to determine whether or not there is a measurement unit of which the apparatus state is "Sample Returning Possible" (Step S112). When at least any one of the state information stored in the measurement unit state data areas S1 and S2 is "Sample Returning Possible" (YES in Step S112), the CPU 51a transports the sample rack L to the one of which the state information is "Sample Returning Possible" among the first measurement unit 2 and the second measurement unit 3 (Step S113). In this process, when "Sample Returning Possible" is stored in the measurement unit state data area S1, the CPU 51a refers to the sample processing table PT, and transport the sample rack L such that the holding position corresponding to the record of which the field F4 is stored with "Sample take-in (first measurement unit)" is changed to the first sample container take-out/returning position 43*a*. In addition, when "Sample Returning Possible" is stored in the measurement unit state data area S2, the CPU 51*a* refers to the sample processing table PT and transports the sample rack L such that the holding position corresponding to the record of which the field F4 is stored with "Sample Take-in (second measurement unit)" is changed to the second sample container take-out/returning position 43*b*. When both the first measurement unit 2 and the second measurement unit 3 are in the state of "Sample Returning Possible", the CPU 51*a* transports the sample rack L by setting the first measurement unit 2 to the transport destination.

Next, the CPU 51*a* performs the sample returning process (Step S114). In this sample returning process, one of the first measurement unit 2 and the second measurement unit 3, which is in the state of "Sample Returning Possible", is controlled, so that the sample container T is discharged from the measurement unit and returns to the sample rack L. In addition, in the sample returning process, the measuring state in the sample processing table PT of the returned sample is changed to "Measured", so that the sample processing table PT is updated. The details of the sample returning process will be described later. After the sample returning process described above is completed, The CPU 51*a* returns the process to Step S103.

In addition, in Step S112, when "Sample Returning Possible" is not stored in both the measurement unit state data areas S1 and S2 (NO in Step S112), the CPU 51*a* refers to the sample processing table PT so as to determine whether or not there is a holding position for which the measuring order is not confirmed, that is, a holding position for which the information "0" indicating no sample is not stored in the field F2 in the sample processing table PT and the information of the measuring order is not stored in the field F3 (see FIG. 10B, Step S115).

In Step S115, when there is a holding position for which the measuring order is not confirmed (YES in Step S115), the CPU 51*a* controls the sample transport unit 4 so as to transport the sample rack L, and positions one at a holding position of the sample rack L, for which the measuring order is not confirmed in the holding position of the corresponding sample rack L, to the reading position 43*d* in front of the bar-code reading section 44 (Step S116). Here, being positioned at the reading position 43*d* is to be positioned at a holding position (a holding position on the downstream end side in the transport direction of the sample rack L) with a smallest number in the holding positions for which "0" is not stored in the field F2 in the sample processing table PT and the information of the measuring order is not stored in the field F3. That is, when there is no sample of which the measuring order is confirmed, the holding position "1" is selected, and the sample rack L is transported such that the holding position "1" becomes the reading position 43*d*. In addition, when the measuring orders of the other samples excepting the sample of which the holding position is "1" are not confirmed, the holding position "2" is selected, and the sample rack L is transported such that the holding position "2" becomes the reading position 43*d*. Therefore, the sample rack is positioned at the reading position 43*d* in the order increasing the number thereof.

When the sample rack L is transported such that the selected holding position becomes the reading position 43*d*, the CPU 51*a* determines whether or not the sample container T is detected by the sample container sensor 45 (Step S117). Here, when the sample container T is detected (YES in Step S117), the sample ID is read from the sample bar-code of the sample container T by the bar-code reading section 44 (Step S118).

Thereafter, the CPU 51*a* performs the measuring order obtaining process as to be described later. In this process, the CPU 51*a* obtains the measuring order of the sample. In addition, the measuring order obtaining process is performed in parallel with the sample transport controlling process by a multitasking process. Therefore, while the measuring order obtaining process is performed, the transportation of the sample rack L becomes possible.

On the other hand, in Step S117, when the sample container T is not detected (NO in Step S117), the CPU 51*a* stores "0" in the cell corresponding to the holding position of the field F2 in the sample processing table PT (Step S119), and returns the process to Step S115.

In addition, in Step S115, when there is no holding position for which the measuring order is not confirmed (NO in Step S115), the CPU 51*a* determines whether or not a new sample rack L can be sent to the rack transport section 43 (Step S120). In Step S120, the CPU 51*a* can transport a new sample rack L when the sample rack L held on the before-analysis rack holding section 41 is detected by a sensor, the fields F2 of all the holding positions before a predetermined holding position (for example, the holding position "7") are stored with any one of "0" and "1" in the sample processing table PT relating to the sample rack L which is being currently transported by the rack transport section 43 (that is, there is no cell set with "NULL"), and "Measured" is stored in the fields F4 in all the records of which the fields F2 are stored with "1". That is, when a new sample rack L is held on the before-analysis rack holding section 41 and the sample at each holding position before a predetermined holding position of the sample rack L being transported is completely taken in and returned, a new sample rack L can be transported. Therefore, even through one sample is positioned at the holding position before a predetermined holding position, when "NULL" is stored in the field F2, or when "Unmeasured" or "Sample Loading" is stored in the field F4, a new sample rack L cannot transported.

In Step S120, when a new sample rack L can be transported (YES in Step S120), the CPU 51*a* secures an area for a new sample processing table in the RAM 51*c* (Step S121). Further, the CPU 51*a* controls the rack sending sections 41*b*, so that a new sample rack L is moved by the before-analysis rack holding section 41 so as to be sent to the rack transport section 43 (Step S122). At this time, the CPU performs a transport control on the transport section 43 in order not to occur interference between the current transported sample rack L and a newly sent sample rack L with each other, and thus the new sample rack L is sent to the rack transport section 43. After completing the process of Step S122, the CPU 51*a* returns the process to Step S103.

On the other hand, in Step S120, when a new sample rack L cannot be transported (NO in Step S120), the CPU 51*a* stands by for a predetermined period of time (for example, 1 sec) (Step S123), and then returns the process to Step S103. The CPU refers to the state queues Q1 and Q2 so as to store data showing the state of the first measurement unit 2 and the second measurement unit 3 at this point of time in the measurement unit state data areas S1 and S2 (Step S103).

In Step S104, when the measuring states of all the samples are "Measured" in the sample processing table PT (YES in Step S104), the CPU 51*a* controls the sample transport unit 4 such that the sample rack L (the left sample rack L when two sample racks L are on the rack transport section 43) is transported to the after-analysis holding section 42 by the rack transport section 43 (see FIG. 10A, Step S124). The CPU releases an area of the sample processing table PT corresponding to the sample rack L, in the RAM 51c (Step S125), and returns the process to Step S103.

<Measuring Order Obtaining Process>

Figure 13:
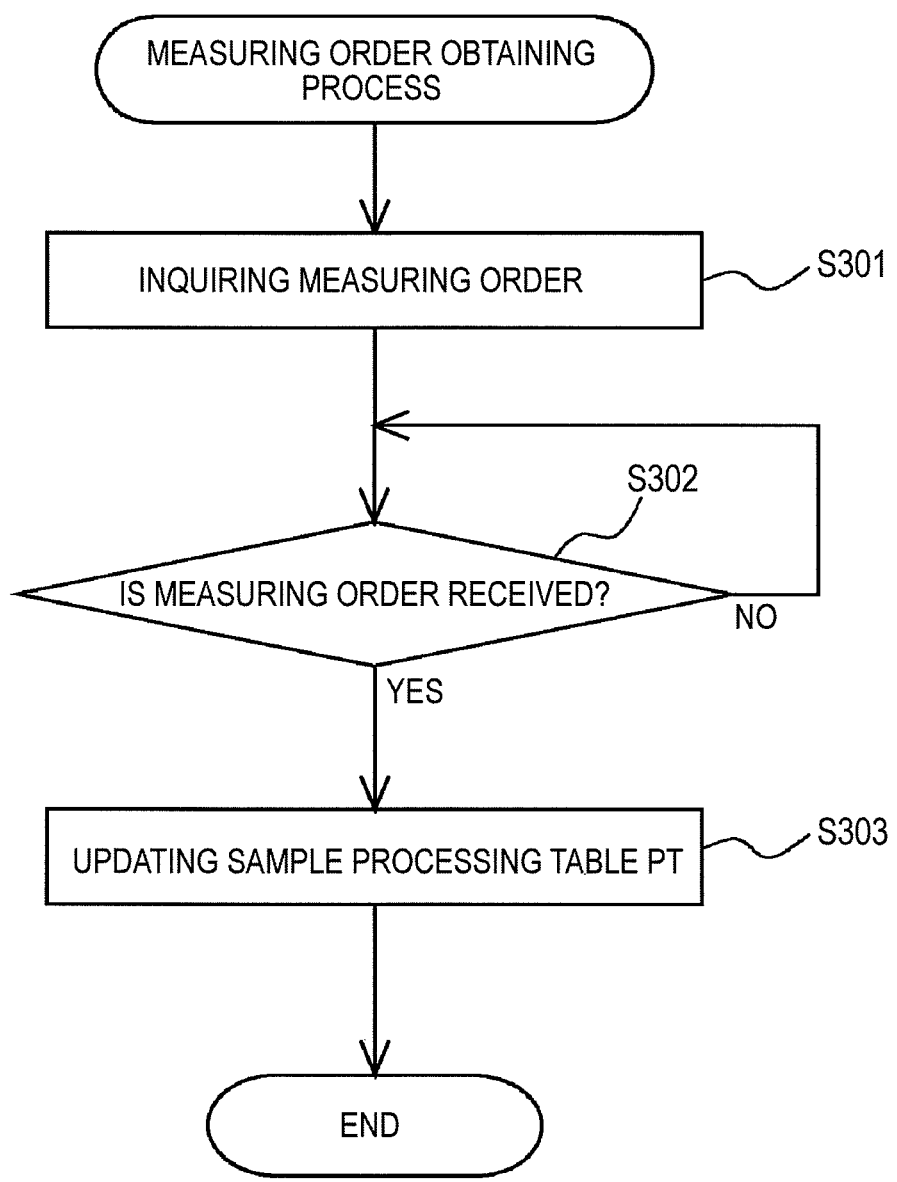
FIG. 13 is a flowchart illustrating the flow of a measuring order obtaining process carried out by a CPU of an information processing unit of a sample processing apparatus.

Next, the measuring order obtaining process carried out by the information processing unit 5 will be described. FIG. 13 is a flowchart illustrating the flow of the measuring order obtaining process carried out by the information processing unit 5 of the sample processing apparatus 1.

In the measuring order obtaining process, the CPU 51a first makes an inquiry to the host computer 6 for the measuring order corresponding to the sample ID (Step S301). The inquiry is carried out by transmitting measuring order request data including the sample ID to the host computer 6 which is connected via a network. The CPU 51a stands by to receive the measuring order (NO in Step S302). When receiving the measuring order (YES in Step S302), the CPU stores "1" in the cell of field F2 which indicates the existence of the sample container corresponding to the holding position, stores the measuring order in the cell of field F3 of the measuring order, and stores the information of the "Unmeasured" in the field F4 of the measuring state in the sample processing table PT, so that the sample processing table PT is updated (Step S303) and the measuring order obtaining process is completed.

The above-mentioned measuring order obtaining process is performed in parallel with the sample transport controlling process by a multitasking process. Therefore, while the measuring order obtaining process is performed, the transportation of the sample rack L becomes possible.

<Sample Take-in Process>

Figure 14:
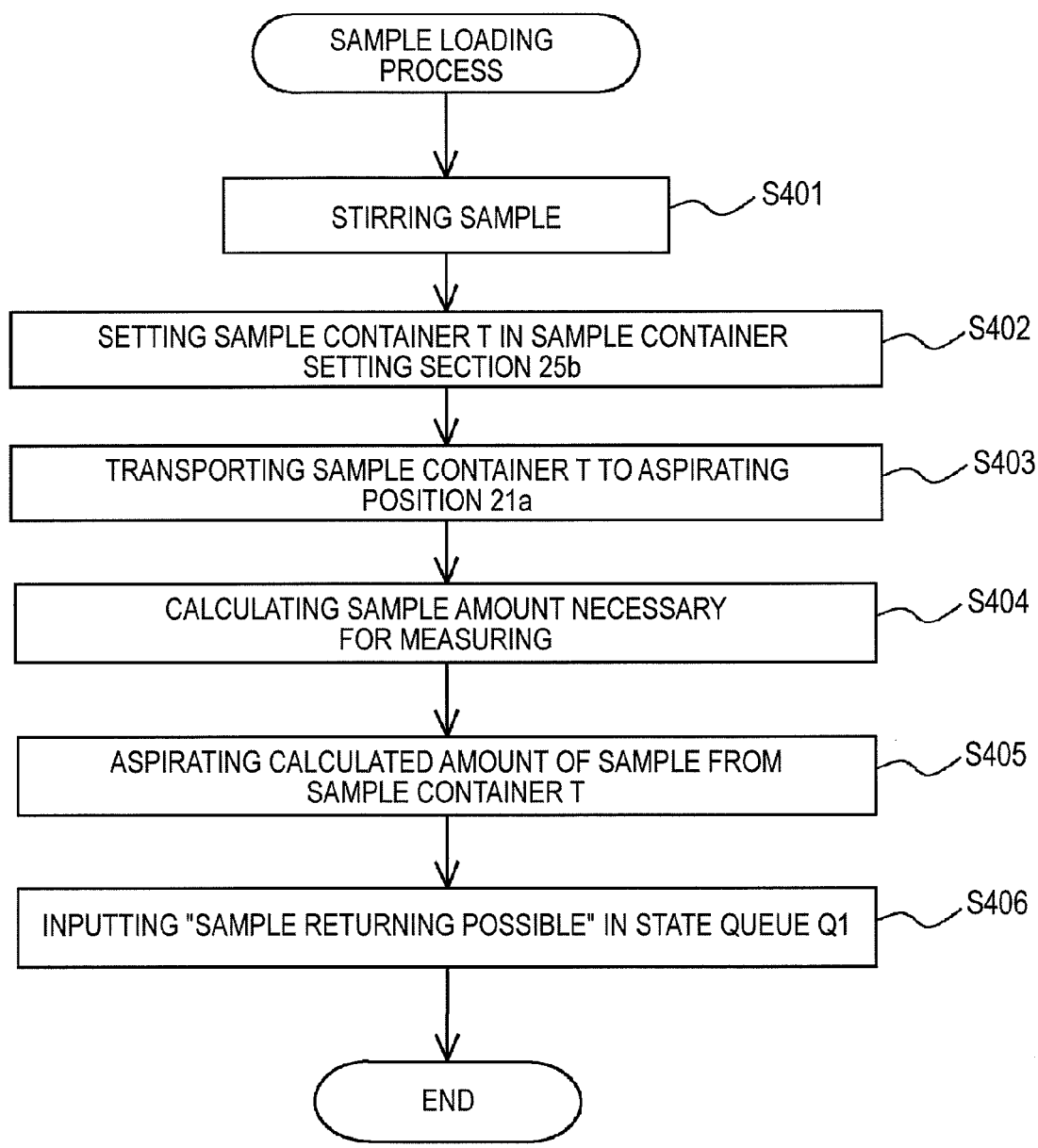
FIG. 14 and FIG. 15 are flowcharts illustrating the flow of a sample taking in process carried out by a CPU of an information processing unit of a sample processing apparatus.

Next, the sample take-in process carried out by the information processing unit 5 will be described. FIG. 14 is a flowchart illustrating the flow of the sample take-in process carried out by the information processing unit 5 of the sample processing apparatus 1. Here, the sample take-in process carried out by the first measurement unit 2 is described, and the sample take-in process carried out by the second measurement unit 3 is also similar thereto.

As described above, after the sample container T positioned at the first sample container—take-out/returning position 43a is pulled out of the sample rack L, the sample take-in process by the first measurement unit 2 is performed by the CPU 51a. In the sample take-in process by the first measurement unit 2, the CPU 51a first controls the hand section 25a to oscillate the sample container T, and thus the sample therein is stirred for a predetermined period of time (Step S401). The stirring of the sample takes a time about tens of seconds. Next, the CPU 51a controls the hand section 25a so as to set the sample container T to the sample container setting section 25b (Step S402), and further controls the sample container transport section 25 so as to transport the sample container T to the aspirating position (Step S403). Further, the CPU 51a refers to the measuring order of the sample to calculate a sample amount required for the measuring from the measurement items (Step S404). Next, the CPU 51a controls the sample aspirating section 21 so as to aspirate an amount necessary for the sample from the sample container T (Step S405). After the process of Step S405 is completed, since the first measurement unit 2 is in a state capable of returning the sample, the CPU 51a inputs the information of the "Sample Returning Possible" in the state queue Q1 (Step S406), and completes the process.

The above-mentioned sample take-in process is performed in parallel with the sample transport controlling process by a multitasking process. Therefore, while the sample take-in process is performed, the transportation of the sample rack L becomes possible.

<Sample Measuring Process>

Figure 15:
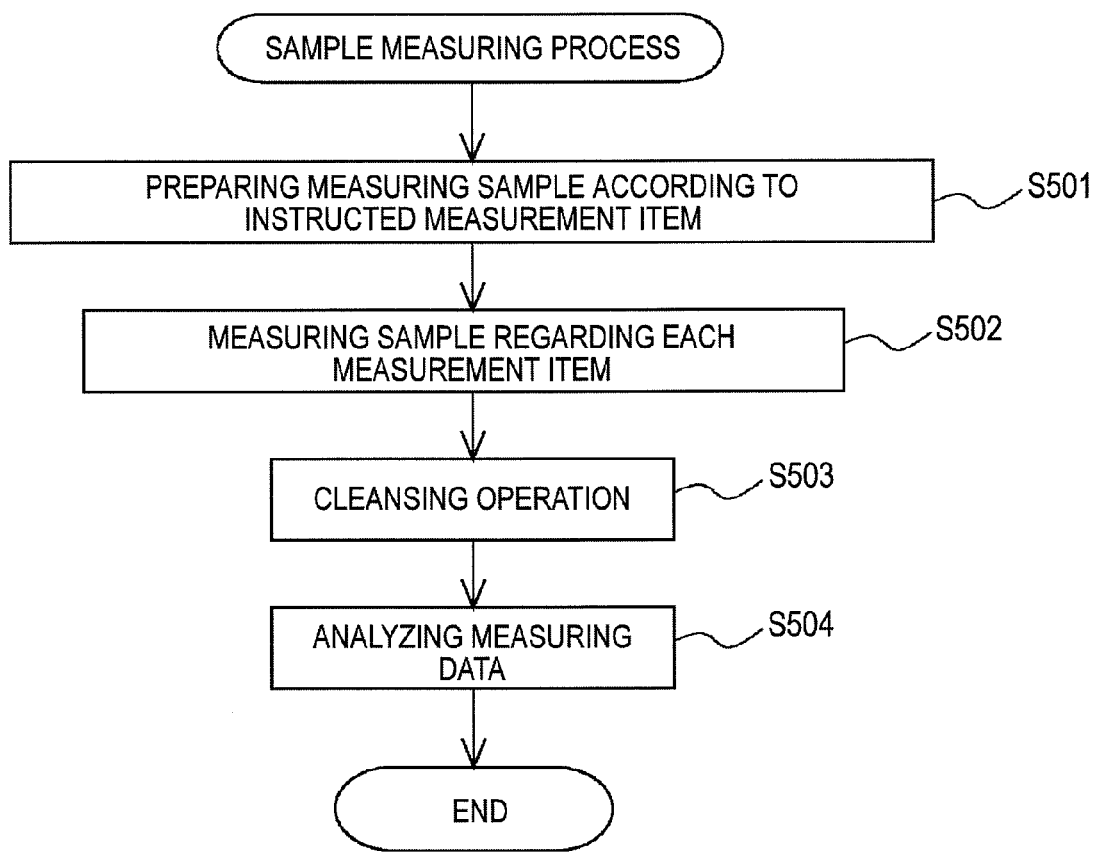

Next, the sample measuring process carried by the information processing unit 5 will be described. FIG. 15 is a flowchart illustrating the flow of the sample measuring process carried by the information processing unit 5 of the sample processing apparatus 1. Here, the sample measuring process carried out by the first measurement unit 2 is described, and the sample measuring process carried out by the second measurement unit 3 is also similar thereto.

After the above-mentioned sample take-in process is completed, the CPU 51a performs the sample measuring process. In the sample measuring process, the CPU 51a first controls the sample preparing section 22 so as to prepare the measuring samples corresponding to the measurement items (Step S501). Next, the CPU 51a supplies the measuring sample to the detecting section 23 so as to carry out the measurement of the sample regarding each measurement item included in the measuring order by the detecting section 23 (Step S502). Therefore, the CPU 51a obtains measurement data output from the detecting section 23. Thereafter, the CPU 51a performs a cleaning operation for cleaning a flow path used for the measurement and a reaction chamber (Step S503).

In addition, the CPU 51a performs an analysis process of the measurement data (Step S504) so as to obtain the analysis result of the numerical values including, such as, RBC, PLT, HGB, WBC, NEUT, LYMPH, EO, BASO, and MONO. After the process of Step S504 is completed, the CPU 51a completes the process.

The above-mentioned sample measuring process is performed in parallel with the sample transport controlling process by a multitasking process. Therefore, while the sample measuring process is performed, the transportation of the sample rack L becomes possible.

<Sample Returning Process>

Figure 16:
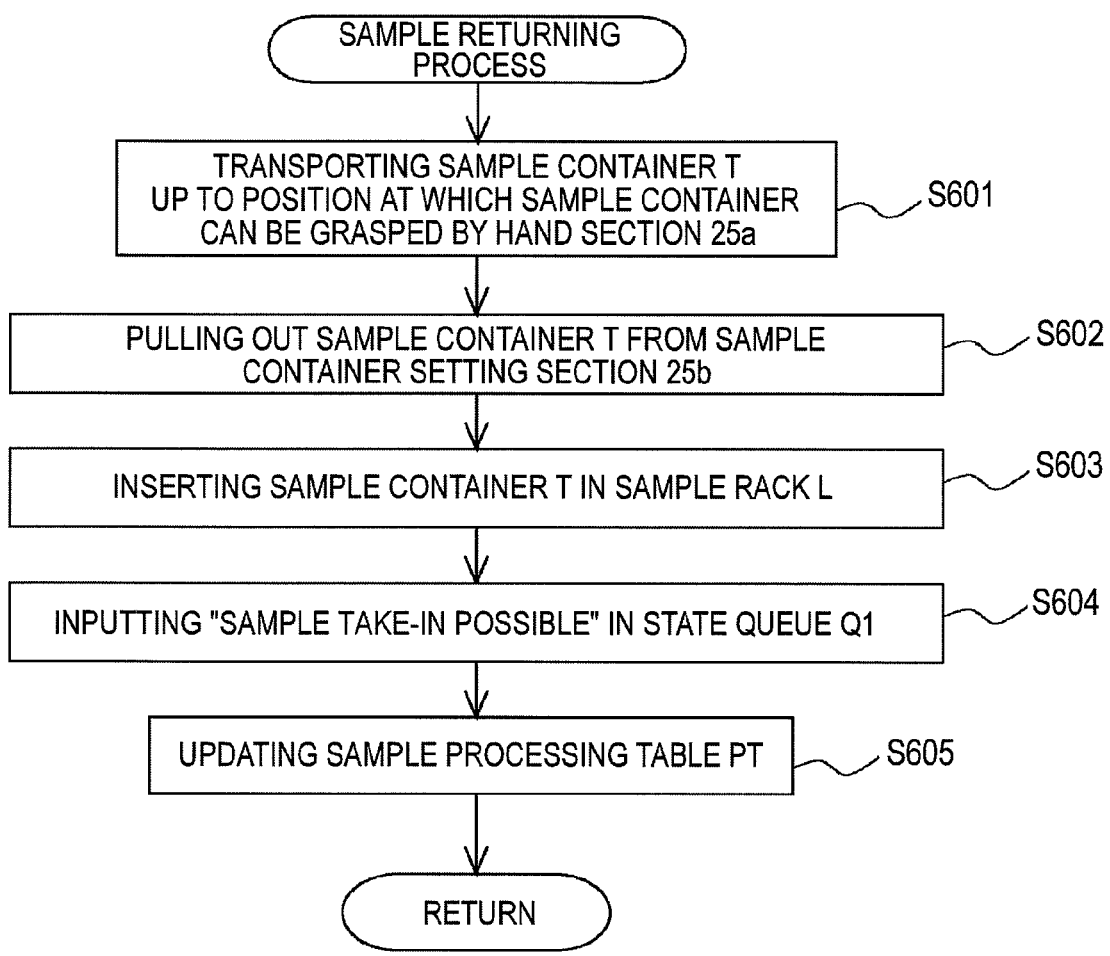
FIG. 16 is a flowchart illustrating the procedure of a sample returning process carried out by a CPU of an information processing unit of a sample processing apparatus.

Next, the sample returning process carried out by the information processing unit 5 will be described. FIG. 16 is a flowchart illustrating the flow of the sample returning process carried out by the information processing unit 5 of the sample processing apparatus 1. Here, the sample returning process carried out by the first measurement unit 2 is described, and the sample returning process carried out by the second measurement unit 3 is also similar thereto.

In the sample returning process, the CPU 51a first controls the sample container transport section 25 and moves the sample container setting section 25b from the aspirating position to be transported up to a position where the sample container T can be grasped by the hand section 25a (Step S601). Next, the CPU 51a controls the hand section 25a so as to grasp the sample container T by the hand section 25a, and then pulls out the sample container T from the sample container setting section 25b (Step S602). Furthermore, the CPU 51a controls the hand section 25a so as to insert the grasped sample container T to the holding position of the sample rack L of the first sample container take-out/returning position 43a (Step S603).

Here, since the first measurement unit 2 becomes in a state where a sample can be taken in, the CPU 51a inputs "Sample Take-in Possible" in the state queue Q1 of the RAM 51c (Step S604). Furthermore, the CPU 51a changes the measuring state in the sample processing table PT of the sample returned to the sample rack L to "Measured" (Step S605). After the process of Step S605 is completed, the CPU 51a returns the process to an invoked address of the sample returning process.

SPECIFIC EXAMPLE

Next, the operation of the above-mentioned sample processing apparatus 1 will be described using a specific example. In the following, the operation of the sample processing apparatus 1 will be described in a case where the sample rack L holding the samples of which the measurement items include the CBC+DIFF item at the holding positions 1 to 10 is put into the sample processing apparatus 1.

Figure 17:
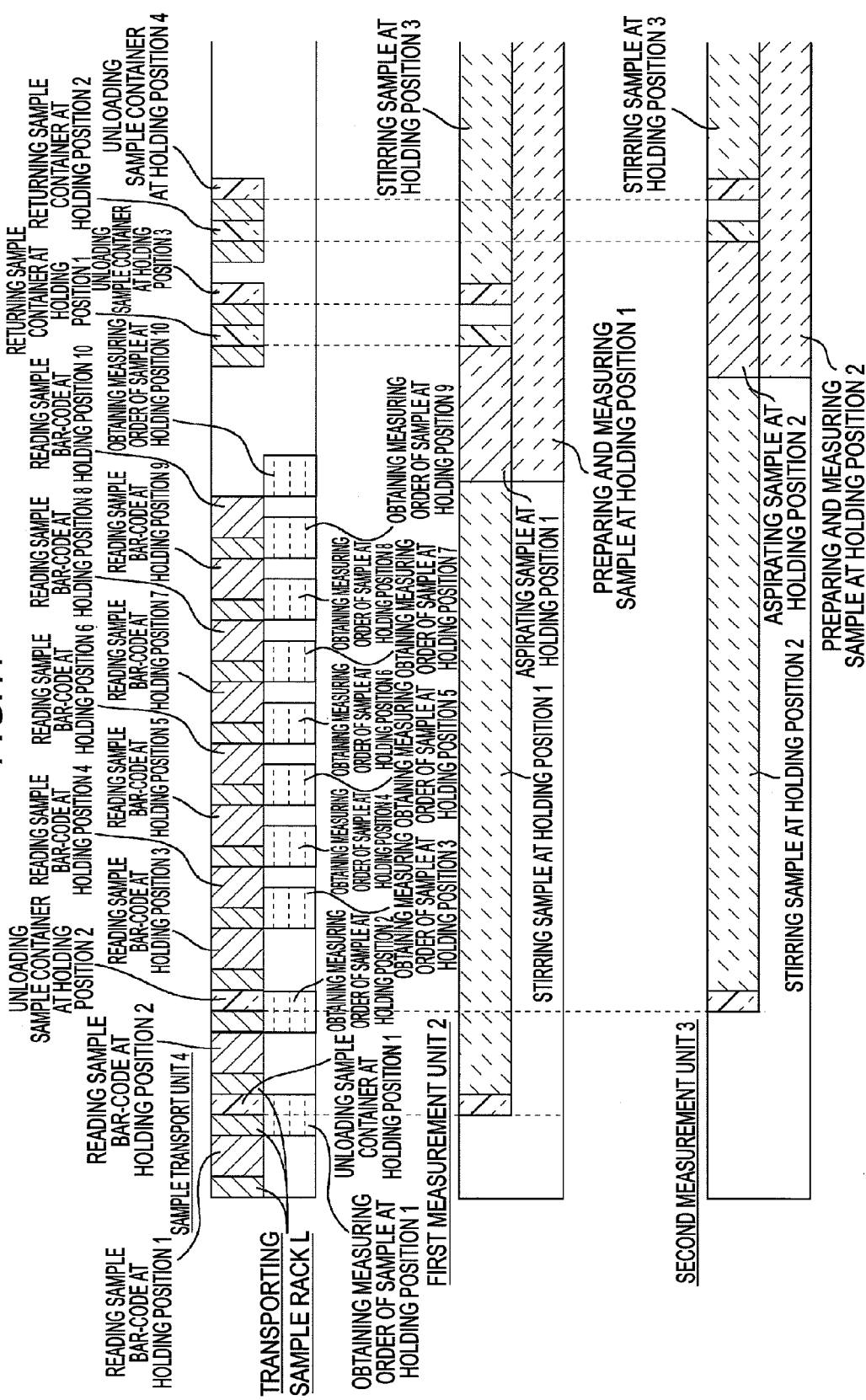
FIG. 17 is a timing chart illustrating the operation of a sample transport unit, a first measurement unit, and a second measurement unit of a sample processing apparatus when a sample rack is put into a sample processing apparatus.
Figure 18B:
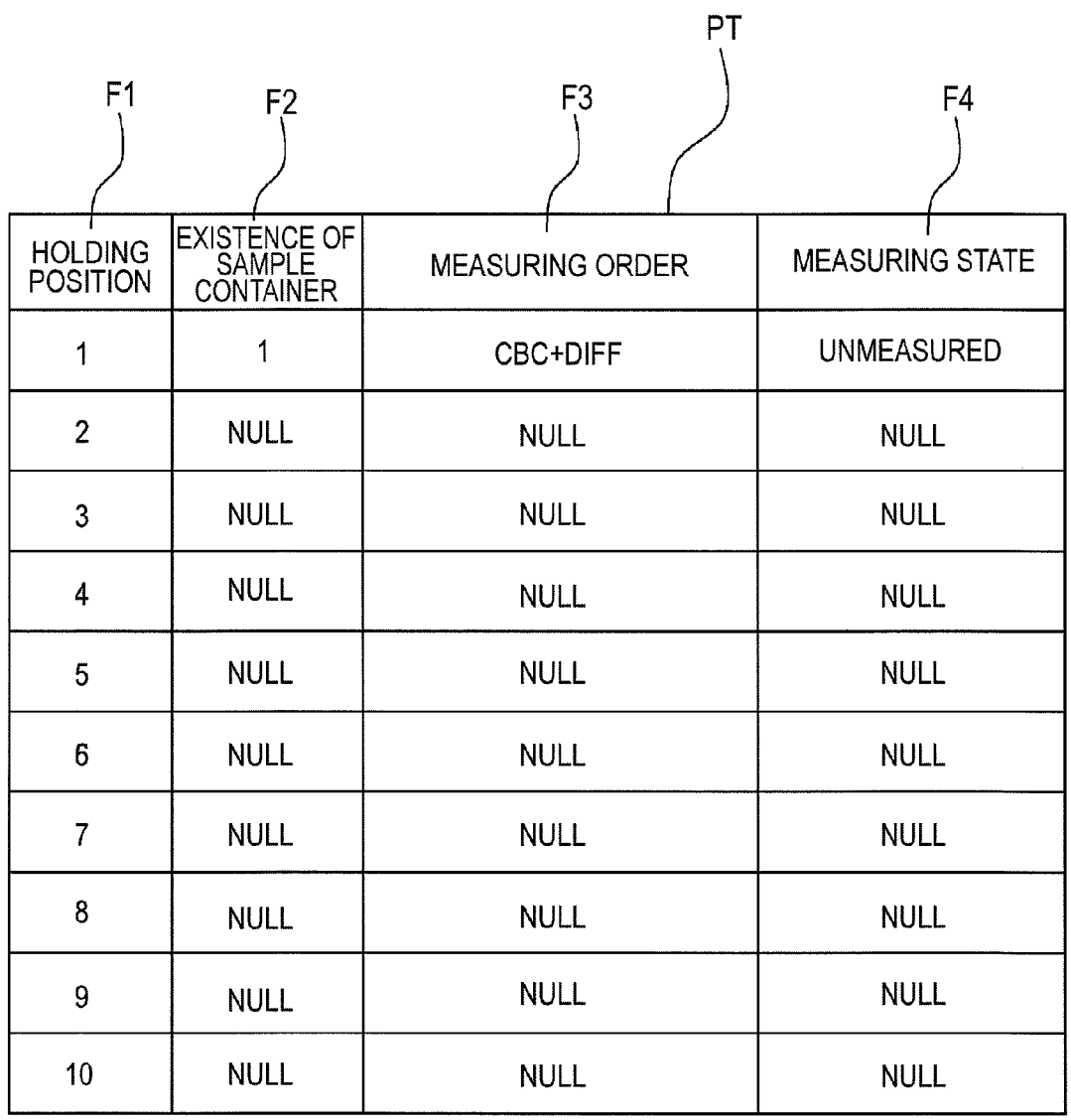

FIG. 17 is a timing chart illustrating the operations of the first measurement unit 2 and the second measurement unit 3 of the sample processing apparatus 1 when the sample rack L is put into the sample processing apparatus 1. First, the sample rack L is put into the before-analysis rack holding section 41, and when the information processing unit 5 is instructed to perform the sample measuring by an operator, the sample rack L held on the before-analysis rack holding section 41 is detected (Step S101 in FIG. 10A), and an area of the sample processing table PT in the information processing unit 5 is secured (Step S102). FIGS. 18A to 18G are diagrams schematically illustrating the state of the sample processing table PT. The state of the sample processing table PT in this point of time is shown in FIG. 18A. In this point of time, the sample processing table PT is in a state where all cells are filled with NULL data excepting the field F1.

Next, the CPU 51a refers to the state queues Q1 and Q2, the finally input data in the state queues Q1 and Q2 is stored in the measurement unit state data areas S1 and S2 (Step S103). Here, since the initial value of "Sample Take-in Possible" is input in both state queues Q1 and Q2, "Sample Take-in Possible" is stored in the respective measurement unit state data areas S1 and S2.

Next, the CPU 51a determines whether or not the sample rack L can be discharged (Step S104). However, since all the fields F2 showing the existence of the sample container of the sample processing table PT are stored with "NULL" (NO in Step S104), the process of the CPU 51a moves to Step S105. In addition, it is determined whether or not there is a necessity-for-process sample in Step S105. However, since there is no necessity-for-process sample in the sample processing table PT (NO in Step S105), the process of the CPU 51a moves to Step S112.

Next, the CPU 51a determines whether or not there is a measurement unit of which the apparatus state is "Sample Returning Possible" (Step S112). Here, since "Sample Take-in Possible" is stored in both the measurement unit state data areas S1 and S2 (NO in Step S112), the process of the CPU 51a moves to Step S115.

The CPU 51a determines whether or not there is a holding position for which the measuring order is not confirmed (Step S115). Here, in the sample processing table PT, there is no record in which the information on the measuring order is stored in the field F3 of the measuring order. That is, there is only samples for which the measuring order is confirmed (YES in Step S115). Therefore, the CPU 51a moves the process to Step S116.

Next, one of the samples accommodated in the sample rack L, its the holding position for which the measuring order is not confirmed, is transported up to the reading position 43d in front of the bar-code reading section 44 (Step S116). Here, since there is no sample for which the measuring order is confirmed at all, the sample rack L is transported until the holding position 1 becomes the reading position 43d. Since the sample container T is held at the holding position 1 of the sample rack L, the sample container T is detected by the sample container sensor 45 (YES in Step S117). Therefore, the sample ID is read from the bar-code of the sample positioned at the holding position 1 by the bar-code reading section 44 (Step S118), and the measuring order obtaining process is performed.

In the measuring order obtaining process, the measuring order of the sample at the holding position 1, that is, the measuring order including the CBC+DIFF item is obtained from the host computer 6 by the CPU 51a (Steps S301 and S302). Then, the sample processing table PT is updated (Step S303). The state of the sample processing table PT at this point of time is shown in FIG. 18B. As shown in the drawing, at the point of time, "1" is stored in the field F2 showing the existence of the sample container T in the row of the holding position 1 of the sample processing table PT, the information representing the "CBC+DIFF" is stored in the field F3 of the measuring order, and the information representing the "Unmeasured" is stored in the field F4 of the measuring state.

As shown in FIG. 17, in parallel with the above-mentioned measuring order obtaining process, the sample transport controlling process is performed continuously. That is, the CPU 51a performs the process of Step S103 again. The CPU 51a refers to the state queues Q1 and Q2, and the finally input data in the state queues Q1 and Q2 is stored in the measurement unit state data areas S1 and S2 (Step S103). Here, since there is no data in the state queues Q1 and Q2, the data of the measurement unit state data areas S1 and S2 is not changed. That is, "Sample Take-in Possible" is stored in each of the measurement unit state data areas S1 and S2.

Next, the process of Step S104 is performed. It is determined whether or not the sample rack L can be discharged, but since the sample rack L cannot be discharged (NO in Step S104), it is determined whether or not there is a necessity-for-process sample in Step S105. Here, the sample at the holding position 1 is the necessity-for-process sample because there is information on the measuring order in the sample processing table PT and the measuring state is "Unmeasured". Therefore, the sample transport destination determining process S106 is performed by the CPU 51a.

In the sample transport destination determining process, first, the CPU 51a selects the necessity-for-process sample of which the number of the holding position is smallest in the sample processing table PT (Step S201). Therefore, the sample at the holding position 1 is selected, and it is determined whether or not the first measurement unit 2 is in the state where the sample can be taken in from the measurement unit state data area S1 of the RAM 51c (Step S202). Here, the information of the "Sample Take-in Possible" is stored in both of the measurement unit state data areas S1 and S2. Therefore, it is determined that the first measurement unit 2 can take in the sample (YES in Step S202), the first measurement unit 2 is determined as the transport destination (Step S203), and the process is returned to an invoked address of the sample transport destination determining process S106.

Next, the CPU 51a determines whether the determined transport destination is the first measurement unit 2 or the second measurement unit 3 (Step S107). Since the transport destination is determined as the first measurement unit 2 (YES in Step S107), the sample at the holding position 1 is transported to the first sample container take-out/returning position 43a (Step S108).

Figure 18C:
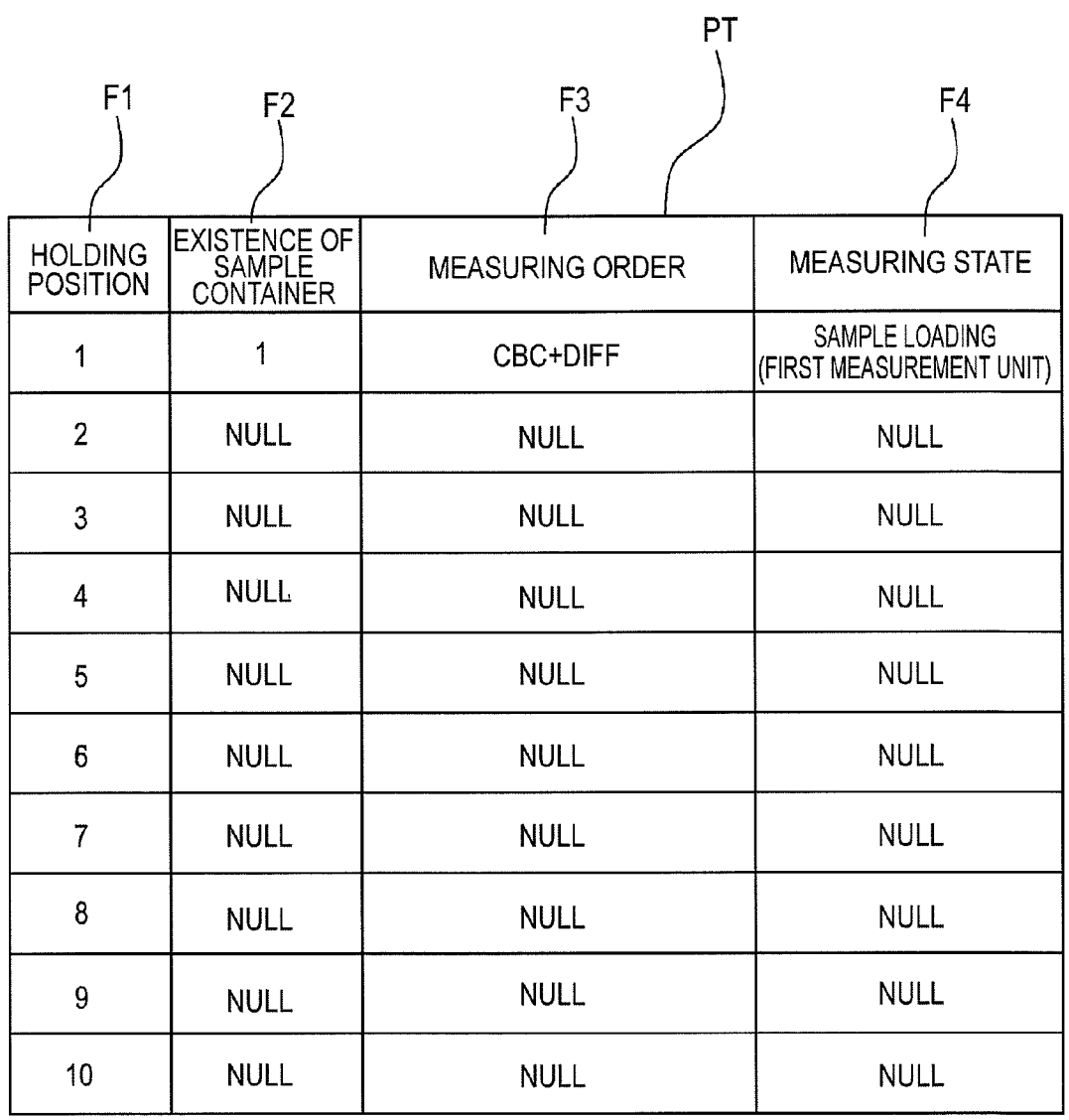

Next, the CPU 51a inputs "Sample Take-in/Returning Impossible" in the state queue Q1 of the RAM 51c (Step S109), and the measuring state of the holding position 1 of the sample processing table PT is changed so as to be "Sample Take-in (first measurement unit)" (Step S110). Then, the sample container T at the holding position 1, which is positioned at the first sample container take-out/returning position 43a, is pulled out of the sample rack L (Step S111). The state of the sample processing table PT at this point of time is shown in FIG. 18C. Thereafter, the sample take-in process is performed by the first measurement unit 2, and the sample container T is taken in the first measurement unit 2 (Steps S401 to S405).

Even in the state where the sample container T at the holding position 1 is pulled out, the sample rack L can be transported. Then, the CPU 51a performs the subsequent processes of Step S103 again for tens of seconds when the sample container T is taken in the first measurement unit 2. At the point of time, since the finally input data in the state queue Q1 is "Sample Take-in/Returning Impossible", the information of the "Sample Take-in/Returning Impossible" is stored in the measurement unit state data area S1 (Step S103). In addition, as shown in FIG. 18C, since "NULL" is stored in the field F2 of the holding positions 2 to 10, the sample rack L cannot be discharged (NO in Step S104), there is not necessity-for-process sample (NO in Step S105), and there is no measurement unit of which the apparatus state is "Sample Returning Possible" (NO in Step S112). Here, since there is a holding position for which the measuring order is not confirmed (YES in Step S115), the holding position 2 of which the number of the holding position for which the measuring order is not confirmed is smallest becomes the reading position 43d (Step S116). Since the sample container T is held at the holding position 2, the sample container T is detected by the sample container sensor 45 (YES in Step S117). Therefore, the sample ID is read from the bar-code of the sample at the holding position 2 by the bar-code reading section 44 (Step S118), and the measuring order obtaining process is performed.

In the measuring order obtaining process, the measuring order of the sample at the holding position 2, that is, the measuring order including the CBC+DIFF item is obtained from the host computer 6 by the CPU 51a (Steps S301 and S302). Then, the sample processing table PT is updated (Step S303). The state of the sample processing table PT at this point of time is shown in FIG. 18D. As shown in the drawing, at the point of time, "1" is stored in the field F2 showing the existence of the sample container T in the row of the holding position 2 of the sample processing table PT, the information representing the "CBC+DIFF" is stored in the field F3 of the measuring order, and the information representing the "Unmeasured" is stored in the field F4 of the measuring state.

As shown in FIG. 17, in parallel with the above-mentioned measuring order obtaining process, the sample transport controlling process is continuously performed. That is, the CPU 51a performs the process of Step S103 again. At the point of time, since there is no data in the state queues Q1 and Q2, the data in the measurement unit state data areas S1 and S2 are not changed in the process of Step S103. That is, "Sample Take-in/Returning Impossible" is stored in the measurement unit state data area S1, and "Sample Take-in Possible" is stored in the measurement unit state data area S2.

In addition, as shown in FIG. 18D, since "NULL" is stored in the field F2 of the holding positions 3 to 10, the sample rack L cannot be discharged (NO in Step S104), and it is determined whether or not there is a necessity-for-process sample in Step S105. Here, since the information of the measuring order exists in the sample processing table PT and the measuring state is "Unmeasured", the sample at the holding position 2 is the necessity-for-process sample. Therefore, the sample transport destination determining process S106 is performed by the CPU 51a.

In the sample transport destination determining process, first, the CPU 51a selects the necessity-for-process sample of which the number of the holding position is smallest in the sample processing table PT (Step S201). Therefore, the sample at the holding position 2 is selected, and it is determined whether or not the first measurement unit 2 is in the state where the sample can be taken in from the measurement unit state data area S1 of the RAM 51c (Step S202). Here, the information of the "Sample Loading/Returning Impossible" is stored in the measurement unit state data area S1. Therefore, it is determined that the first measurement unit 2 cannot take in the sample (NO in Step S202), it is determined whether or not the second measurement unit 3 is in a state where the sample can be taken in from the measurement unit state data area S2 of the RAM 51c (Step S204). Here, the information of the "Sample Loading Possible" is stored in the measurement unit state data area S2. Therefore, it is determined that the second measurement unit 3 can take in the sample (YES in Step S204), the second measurement unit 3 is determined as the transport destination (Step S205), and the process is returned to an invoked address of the sample transport destination determining process S106.

Next, the CPU 51a determines whether the determined transport destination is the first measurement unit 2 or the second measurement unit 3 (Step S107). Since the transport destination is determined as the second measurement unit 3 (YES in Step S107), the sample at the holding position 2 is transported to the second sample container take-out/returning position 43b (Step S108).

Figure 18E:
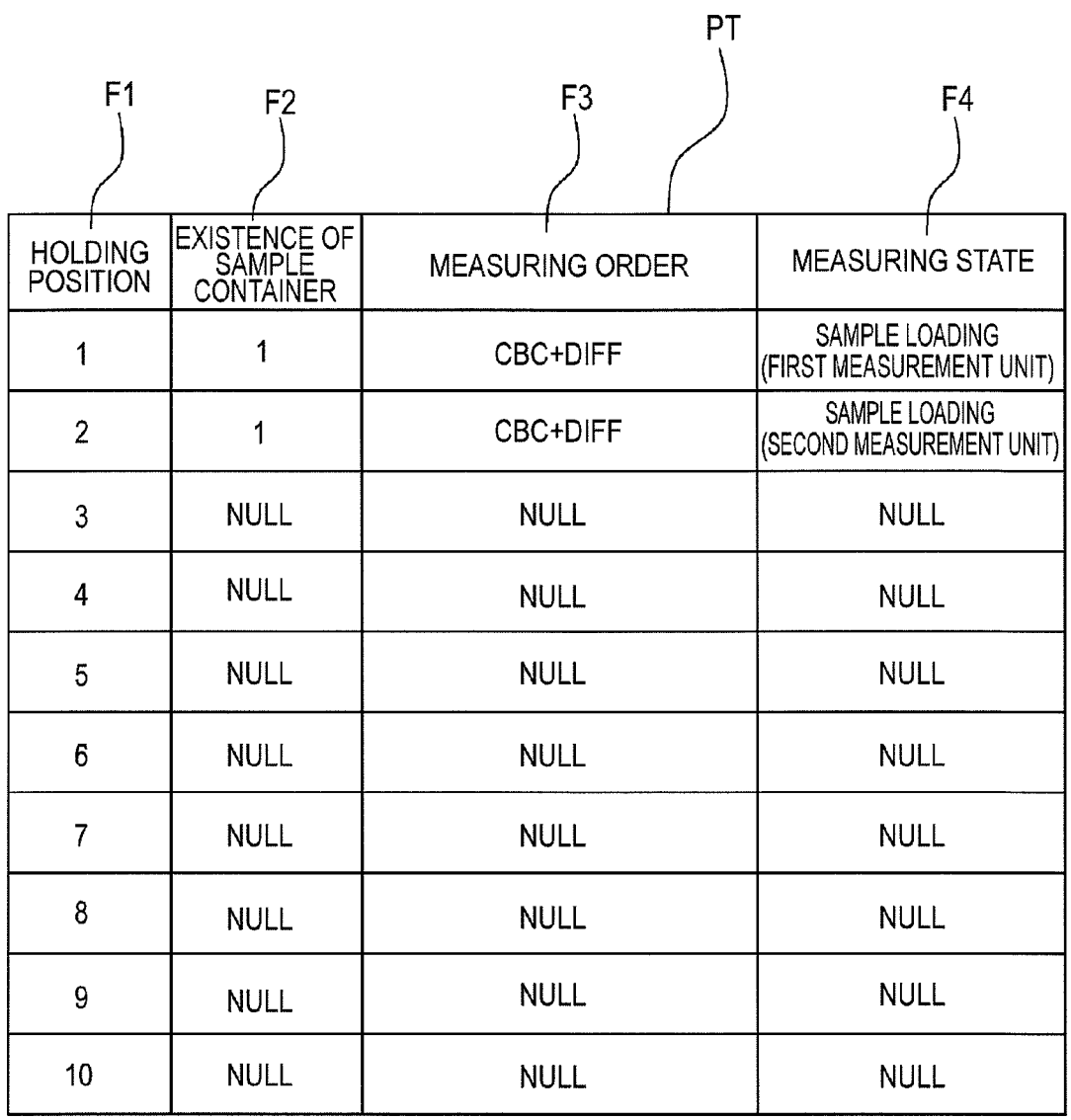

Next, the CPU 51a inputs "Sample Take-in/Returning Impossible" in the state queue Q2 of the RAM 51c (Step S109), and the measuring state of the holding position 2 of the sample processing table PT is changed so as to be "Sample Take-in (second measurement unit)" (Step S110). Then, the sample container T at the holding position 2, which is positioned at the second sample container take-out/returning position 43b, is pulled out of the sample rack L (Step S111). The state of the sample processing table PT at this point of time is shown in FIG. 18E. Thereafter, the sample take-in process is performed by the second measurement unit 3, and the sample container T is taken in the second measurement unit 3 (Steps S401 to S405). Further, as shown in FIG. 17, the above-mentioned sample obtaining process of the sample container T at the holding position 1 is also performed in parallel therewith.

It takes a time about tens of seconds until the above-mentioned loading of the sample container T is completed. The CPU 51a keeps on the sample transport controlling process during the above-mentioned sample take-in process is performed on the sample at the holding positions 1 and 2. In addition, when the sample take-in is completed, the sample measuring process is performed. The sample measuring process is also performed in parallel with the sample transport controlling process.

The CPU 51a performs the subsequent processes of Step S103 again during the sample take-in process is performed by the first measurement unit 2 and the second measurement unit 3. At the point of time, since the finally input data in the state queue Q2 is "Sample Take-in/Returning Impossible", the information of the "Sample Take-in/Returning Impossible" is stored in the measurement unit state data area S2. On the other hand, since no data is input in the state queue Q1, the data stored in the measurement unit state data area S1 remains in "Sample Take-in/Returning Impossible", and is not changed (Step S103).

As shown in FIG. 18E, since the information representing the existence of the sample container T at the holding positions 3 to 10 in the sample processing table PT is "NULL", the sample rack L cannot be discharged (NO in Step S104). Since there is no necessity-for-process sample (NO in Step S105) and the measuring order of the sample at the holding positions 3 to 10 is not confirmed (YES in Step S115), the holding position 3 of which the number of the holding position for which the measuring order is not confirmed is smallest becomes the reading position 43*d* (Step S116). Since the sample container T is held on the holding position 3, the sample container T is detected by the sample container sensor 45 (YES in Step S117). Therefore, the sample ID is read from the bar-code of the sample at the holding position 3 by the bar-code reading section 44 (Step S118), and the measuring order obtaining process is performed.

Figure 18F:
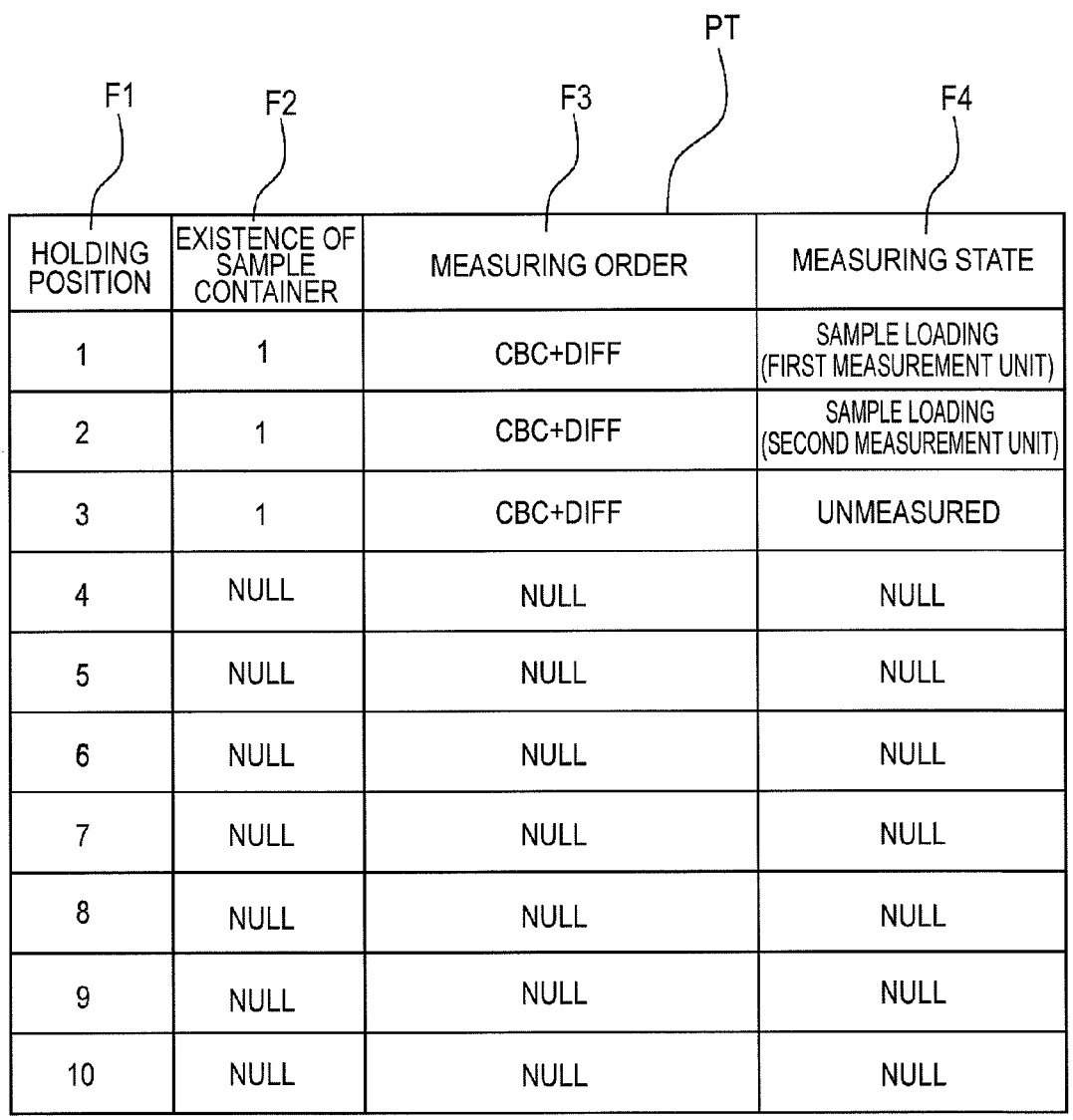

In the measuring order obtaining process, the measuring order of the sample at the holding position 3, that is, the measuring order including the CBC+DIFF item is obtained from the host computer 6 by the CPU 51*a* (Steps S301 and S302). Then, the sample processing table PT is updated (Step S303). The state of the sample processing table PT at this point of time is shown in FIG. 18F. As shown in the drawing, at the point of time, "1" is stored in the field F2 showing the existence of the sample container T in the row of the holding position 3 of the sample processing table PT, the information representing the "CBC+DIFF" is stored in the field F3 of the measuring order, and the information representing the "Unmeasured" is stored in the field F4 of the measuring state.

As shown in FIG. 17, in parallel with the above-mentioned measuring order obtaining process, the sample transport controlling process is continuously performed. That is, the CPU 51*a* performs the process of Step S103 again. At the point of time, since there is no data in the state queues Q1 and Q2, the data of the measurement unit state data areas S1 and S2 is not changed in the process of Step S103. That is, "Sample Take-in/Returning Impossible" is stored in each of the measurement unit state data areas S1 and S2.

As shown in FIG. 18F, since the information representing the existence of the sample container T at the holding positions 4 to 10 becomes "NULL" (NO in Step S104), it is determined whether or not there is a necessity-for-process sample in Step S105. Here, the sample at the holding position 3 is the necessity-for-process sample because there is information on the measuring order in the sample processing table PT and the measuring state is "Unmeasured". Therefore, the sample transport destination determining process S106 is performed by the CPU 51*a*.

In the sample transport destination determining process, first, the CPU 51*a* selects the necessity-for-process sample of which the number of the holding position is smallest in the sample processing table PT (Step S201). Therefore, the sample at the holding position 3 is selected, and it is determined whether or not the first measurement unit 2 is in the state where the sample can be taken in from the measurement unit state data area S1 of the RAM 51*c* (Step S202). Here, the information of the "Sample Take-in/Returning Impossible" is stored in the measurement unit state data areas 51. Therefore, it is determined that the first measurement unit 2 cannot take in the sample (NO in Step S202), it is determined whether or not the second measurement unit 3 is in a state where the sample can be taken in from the measurement unit state data area S2 of the RAM 51*c* (Step S204). Here, the information of the "Sample Take-in/Returning Impossible" is stored in the measurement unit state data area S2. Therefore, the CPU 51*a* determines that the second measurement unit 3 cannot take in the sample (NO in Step S204), determines that the transport destination is "NO" (S206), and returns the process to an invoked address of the sample transport destination determining process.

Next, the CPU 51*a* determines whether the determined transport destination is the first measurement unit 2 or the second measurement unit 3 (Step S107). Since the determined transport destination is "NO" (NO in Step S107), the CPU determines whether or not there is a measurement unit of which the apparatus state is "Sample Returning Possible" (Step S112). Here, since "Sample Take-in/Returning Impossible" is stored in both the measurement unit state data areas S1 and S2 (NO in Step S112), the CPU 51*a* refers to the sample processing table PT so as to determine whether or not there is a holding position for which the measuring order is not conformed (Step S115). Here, since the measuring orders of the holding positions 4 to 10 are not confirmed (YES in Step S115), the holding position 4 with the smallest number among the holding positions for which the measuring order is not confirmed is positioned at the reading position 43*d* (Step S116). Since the sample container T is held on the holding position 4, the sample container T is detected by the sample container sensor 45 (YES in Step S117). Therefore, the sample ID is read from the bar-code of the sample at the holding position 4 by the bar-code reading section 44 (Step S118), and the measuring order obtaining process is performed.

In the measuring order obtaining process, the measuring order of the sample at the holding position 4, that is, the measuring order including the CBC+DIFF item is obtained from the host computer 6 by the CPU 51*a* (Steps S301 and S302). Then, the sample processing table PT is updated (Step S303). "1" is stored in the field F2 showing the existence of the sample container T in the row of the holding position 4 of the sample processing table PT, the information representing the "CBC+DIFF" is stored in the field F3 of the measuring order, and the information representing the "Unmeasured" is stored in the field F4 of the measuring state.

As shown in FIG. 17, in parallel with the above-mentioned measuring order obtaining process, the sample transport controlling process is continuously performed. The subsequent processes of Step S103 are repeatedly performed, and the measuring orders of the sample at the other holding positions 5 to 10 are obtained (Steps S103 to S118 and S301 to S303). As described above, the updated sample processing table PT is shown in FIG. 18G.

In addition, in the middle of reading the sample bar-codes and obtaining the measuring orders with respect to the samples at the above-mentioned holding positions 3 to 10, when the sample obtaining process relating to the sample container T at the holding position 1 (or 2) is completed, the information of the "Sample Returning Possible" is input in the state queue Q1 (or Q2) (Step S406). Therefore, the CPU 51*a* directly stores the information of the "Sample Returning Possible" in the measurement unit state data area S1 (or S2), the sample rack L is transported to the first measurement unit 2 (or the second measurement unit 3) (Step S113), and the sample returning process is performed by the first measurement unit 2 (or the second measurement unit 3) (Step S114). As a result, the sample container T is returned to the holding position 1 (or 2) of the sample rack L. After the sample container T is returned to the sample rack L, the reading of the sample bar-code is restarted, and the sample bar-codes of the samples at the other holding positions are read.

Further, in this example, before the sample take-in process is completed on the holding positions 1 and 2, the reading of the sample bar-codes at the holding positions 3 to 10 and the obtaining of the measuring orders are assumed as being completed.

Thereafter, when the process of Step S405 is completed on the sample container T at the holding position 1, the CPU 51*a* input the information of the "Sample Returning Possible" in the state queue Q1 (Step S406). Further, the CPU 51*a* stores the information of the "Sample Returning Possible", which is finally input in the state queue Q1, in the measurement unit state data area S1 (Step S103). In addition, as shown in FIG. 18G, since the data of the measuring state corresponding to the holding positions 1 and 2 is "Sample Take-in" and the data of the measuring state of the holding positions 3 to 10 is "Unmeasured", the sample rack L cannot be discharged (NO in Step S104). In addition, the samples of the holding positions 3 to 10 are the necessity-for-process samples because there is information on the measuring order in the sample processing table PT and the measuring state is "Unmeasured" (YES in Step S105). Therefore, the sample transport destination determining process S106 is performed by the CPU 51a.

In the sample transport destination determining process, first, in Step S201, the CPU 51a selects the sample at the holding position 3. Next, the information of the "Sample Returning Possible" is stored in the measurement unit state data area S1 of the RAM 51c, and the information of the "Sample Take-in/Returning Impossible" is stored in the measurement unit state data area S2. Therefore, it is determined that both the first measurement unit 2 and the second measurement unit 3 cannot take in the sample (NO in Steps S202 and S204), "NO" is determined as the transport destination (Step S206), and the process is returned to an invoked address of the sample transport destination determining process S106.

Next, the CPU 51a determines whether the determined transport destination is the first measurement unit 2 or the second measurement unit 3 (Step S107). Since the determined transport destination is "NO" (NO in Step S107), the CPU determines whether or not there is a measurement unit of which the apparatus state is "Sample Returning Possible" (Step S112). Here, since "Sample Returning Possible" is stored in the measurement unit state data area S1 (YES in Step S112), the CPU 51a refers to the sample processing table PT so as to transport the sample rack L such that the holding position 1 corresponding to the record in which "Sample Take-in (first measurement unit)" is stored in the field F4 becomes the first sample container take-out/returning position 43a (Step S113).

Next, the CPU 51a performs the sample returning process by the first measurement unit 2 (Step S114). Therefore, the first measurement unit 2 is controlled, so that the accommodated sample container T is discharged from the first measurement unit 2 and returned to the sample rack L (Steps S601 to S603). In addition, the CPU 51a inputs "Sample Take-in Possible" in the state queue Q1 of the RAM 51c (Step S604), and changes the data of the measuring state corresponding to the holding position 1 in the sample processing table PT with "Measured" (Step S605). Thereafter, the CPU 51a returns the process to an invoked address of the sample returning process.

The CPU 51a performs the process of Step S103 again. At the point of time, the finally input data in the state queue Q1 is "Sample Take-in Possible", so that in Step S103, the information of the "Sample Take-in Possible" is stored in the measurement unit state data area S1. That is, "Sample Take-in Possible" is stored in the measurement unit state data area S1, and "Sample Take-in/Returning Impossible" is stored in the measurement unit state data area S2.

At the point of time, the data of the measuring state corresponding of the holding position 2 is "Sample Take-in", and the sample rack L cannot be discharged because the data of the measuring states of the holding positions 3 to 10 are "Unmeasured" (NO in Step S104). In addition, the samples at the holding positions 3 to 10 are the necessity-for-process samples because there is information on the measuring order in the sample processing table PT and the measuring state is "Unmeasured" (YES in Step S105). Therefore, the sample transport destination determining process S106 is performed by the CPU 51a.

In the sample transport destination determining process, first, in Step S201, the CPU 51a selects the sample at the holding position 3. Here, the information of the "Sample Take-in Possible" is stored in the measurement unit state data area S1. Therefore, it is determined that the first measurement unit 2 can take in the sample (YES in Step S202), the first measurement unit 2 is determined as the transport destination (Step S203), and the process is returned to an invoked address of the sample transport destination determining process S106.

Next, the CPU 51a determines whether the determined transport destination is the first measurement unit 2 or the second measurement unit 3 (Step S107). Since the transport destination is determined as the first measurement unit 2 (YES in Step S107), the sample at the holding position 3 is transported to the first sample container take-out/returning position 43a (Step S108).

Next, the CPU 51a inputs "Sample Take-in/Returning Impossible" in the state queue Q1 of the RAM 51c (Step S109), and changes the measuring state of the holding position 3 in the sample processing table PT with "Sample Take-in (first measurement unit)" (Step S110). Then, the sample container T of the holding position 3 at the first sample container take-out/returning position 43a is pulled out from the sample rack L (Step S111). Thereafter, the sample take-in process is performed by the first measurement unit 2, and the sample container T is taken in the first measurement unit 2 (Steps S401 to S405). Further, as shown in FIG. 17, the above-mentioned sample obtaining process of the sample container T at the holding position 2 is also performed in parallel therewith.

Thereafter, when the process of Step 405 is completed on the sample container T at the holding position 2, the CPU 51a inputs the information of the "Sample Returning Possible" in the state queue Q2 (Step S406), and performs the sample measuring process. Further, the CPU 51a stores the information of the "Sample Returning Possible" which is finally input in the state queue Q2 in the measurement unit state data area S1 (Step S103). In addition, since the data of the measuring states corresponding of the holding positions 2 and 3 is "Sample Take-in", and the data of the measuring states of the holding positions 4 to 10 is "Unmeasured", the sample rack L cannot be discharged (NO in Step S104). In addition, the samples at the holding positions 4 to 10 are the necessity-for-process samples because there is information on the measuring order in the sample processing table PT and the measuring state is "Unmeasured" (YES in Step S105). Therefore, the sample transport destination determining process S106 is performed by the CPU 51a.

In the sample transport destination determining process, first, the CPU 51a selects the sample at the holding position 4 in Step S201. Next, the information of the "Sample Take-in/Returning Impossible" is stored in the measurement unit state data area S1 of the RAM 51c, and the information of the "Sample Returning Possible" is stored in the measurement unit state data area S2. Therefore, it is determined that both the first measurement unit 2 and the second measurement unit 3 cannot take in the sample (NO in Steps S202 and S204), and "NO" is determined as the transport destination (Step S206), and the process is returned to an invoked address of the sample transport destination determining process S106.

Next, the CPU 51a determines whether the determined transport destination is the first measurement unit 2 or the second measurement unit 3 (Step S107). Since the determined transport destination is "NO" (NO in Step S107), the CPU determines whether or not there is a measurement unit of which the apparatus state is "Sample Returning Possible" (Step S112). Here, since "Sample Returning Possible" is stored in the measurement unit state data area S2 (YES in Step S112), the CPU 51a refers to the sample processing table PT so as to transport the sample rack L such that the holding position 2 corresponding to the record in which "Sample Take-in (second measurement unit)" is stored in the field F4 becomes the second sample container take-out/returning position 43b (Step S113).

Next, the CPU 51a performs the sample returning process by the second measurement unit 3 (Step S114). Therefore, the second measurement unit 3 is controlled, so that the accommodated sample container T is discharged from the second measurement unit 3 and returned to the sample rack L (Steps S601 to S603). In addition, the CPU 51a inputs "Sample Take-in Possible" in the state queue Q2 of the RAM 51c (Step S604), and changes the data of the measuring state corresponding to the holding position 2 in the sample processing table PT with "Measured" (Step S605). Thereafter, the CPU 51a returns the process to an invoked address of the sample returning process.

Thereafter, similarly to the holding positions 1 to 3, take-in of the sample container T at the holding position 4 by the second measurement unit 3, measuring of the sample at the holding position 3 by the first measurement unit 2, returning of the sample container T at the holding position 3 from the first measurement unit 2, take-in of the sample container T at the holding position 5 by the first measurement unit 2, measuring of the sample at the holding position 4 by the second measurement unit 3, returning of the sample container T at the holding position 4 from the second measurement unit 3, take-in of the sample container T at the holding position 6 by the second measurement unit 3, measuring of the sample at the holding position 5 by the first measurement unit 2, returning of the sample container T at the holding position 5 from the first measurement unit 2, take-in of the sample container T at the holding position 7 by the first measurement unit 2, measuring of the sample at the holding position 6 by the second measurement unit 3, returning of the sample container T at the holding position 6 from the second measurement unit 3, take-in of the sample container T at the holding position 8 by the second measurement unit 3, measuring of the sample at the holding position 7 by the first measurement unit 2, returning of the sample container T at the holding position 7 from the first measurement unit 2, take-in of the sample container T at the holding position 9 by the first measurement unit 2, measuring of the sample at the holding position 8 by the second measurement unit 3, returning of the sample container T at the holding position 8 from the second measurement unit 3, take-in of the sample container T at the holding position 10 by the second measurement unit 3, measuring of the sample at the holding position 9 by the first measurement unit 2, returning of the sample container T at the holding position 9 from the first measurement unit 2, measuring of the sample at the holding position 10 by the second measurement unit 3, and returning of the sample container T at the holding position 10 from the second measurement unit 3 are performed in this order while the processes are partially overlapped with each other.

According to the configuration as described above, while one sample container T is being taken in the first measurement unit 2 (or the second measurement unit 3), the sample rack L is transported, and the processes such as returning of another sample container T, detecting the existence of another sample container T whose sample bar-code is a subject to be read, reading the sample bar-code by the bar-code reader 44, and taking another sample container T in the second measurement unit 3 (or the first measurement unit 2) can be performed. Therefore, wherever one sample container T and another sample container T are held by the sample rack L, the processes such as returning the another sample container T, detecting the existence of the another sample container T, reading the sample bar-code of the another sample container T by the bar-code reader 44, and taking the another sample container T in the second measurement unit 3 (or the first measurement unit 2) can be performed.

Therefore, in the sample processing apparatus 1, the bar-code reading position 43d and the second sample container take-out/returning position 43b (or the first sample container take-out/returning position 43a) can be freely disposed with respect to the first sample container take-out/returning position 43a (or the second sample container take-out/returning position 43b for taking the sample container T in the second measurement unit 3) for taking the sample container T in the first measurement unit 2, and the flexibility in design of the sample processing apparatus 1 is significantly increased.

In addition, according to the configuration as described above, as shown in FIG. 17, it can be known that a time is not wasted but carrying out the take-in of the first measurement unit 2, the second measurement unit 3 and the sample; the returning of the sample container T; the detecting of the sample container T; the reading of the sample bar-code; or the measuring of the sample during the first measurement unit 2 starts to take in the sample at the holding position 1 and then until the measuring of the sample at the holding position 10 is completed by the second measurement unit 3, so that the measurement of the sample is efficiently carried out.

In addition, the sample processing apparatus 1 is configured to carry out the detecting of the sample container T and the reading of the sample bar-code with respect to the plural holding positions of the sample rack L while carrying out the take-in of one sample by the first measurement unit 2 (or the second measurement unit 3). Therefore, compared with the configuration in which the reading of the identification information (sample ID) only with respect to the sample container which is positioned at a predetermined position from the position of the sample while one sample is taken in as in the related art, the process of the sample can be carried out with efficiency.

In addition, in the sample processing apparatus 1, the first sample container take-out/returning position 43a and the second sample container take-out/returning position 43b for taking the sample container T in respect to the first measurement unit 2 and the second measurement unit 3 also serve as the positions for returning the sample container T from the first measurement unit 2 and the second measurement unit 3 to the sample rack L. For this reason, there is no need to provide the position for taking in the sample container T separately from the position for returning the sample container T, so that the sample processing apparatus 1 can be compactly configured.

In addition, the sample processing apparatus 1 is configured such that after the information processing unit 5 determines whether or not the first measurement unit 2 or the second measurement unit 3 is in the state where it can take in the sample, the sample rack L is transported to the measurement unit which is in the state where it can take in the sample, and the sample container T can be taken in the measurement unit. Therefore, after the sample rack L is transported to the measurement unit, there is no need to stand by until the measurement unit comes to be in the state where it can take in the sample, so that the sample can be more efficiently processed.

In addition, the sample processing apparatus 1 is configured such that while the sample container T is taken in the first measurement unit 2 or the second measurement unit 3, the sample container is oscillated in the first measurement unit 2 or the second measurement unit 3 so as to stir the sample. Since the stirring of the sample takes a time about tens of seconds, while the sample take-in process including the stirring process of the sample as described above is being performed by the first measurement unit 2 or the second measurement unit 3, the sample processing apparatus 1 can carry out the process of the sample with efficiency by transporting the sample rack L and performing the process on another sample container T which is held on the sample rack L.

(Other Embodiments)

Further, in the above-mentioned embodiment, the sample processing apparatus 1 has been configured to be provided with two measurement units, that is, the first measurement unit 2 and the second measurement unit 3. However, the present invention is not limited thereto. For example, the sample processing apparatus may be configured such that three or more measurement units are provided, and the sample rack L is transported so as to process another sample container while carrying out the take-in the sample in at least one of the plural measurement units. In addition, the sample processing apparatus may be configured to be provided with a single measurement unit.

In addition, in the above-mentioned embodiment, the sample processing apparatus 1 has been described as the multiple blood cell analyzing apparatus. However, the present invention is not limited thereto. For example, in a biological sample processing apparatus other than the multiple blood cell analyzing apparatus, such as a blood coagulation measuring apparatus, an immune assay analyzing apparatus, a urine material component analyzing apparatus, a urine qualitative analyzing apparatus, or a blood cell smear slide preparing apparatus, another sample container in the sample rack may be processed while the sample container T is being taken in the apparatus.

In addition, in the above-mentioned embodiment, the example has been described in which when the sample container T of the sample rack L at the first sample container take-out/returning position 43a is taken-out, the sample rack L is transported to the second sample container take-out/returning position 43b, and as a process for another sample container T accommodated in the sample rack L, the reading of the bar-code label BL1, the detecting of the existence of the sample container T, and take-out of the sample container T for aspirating the sample by the second measurement unit 3 are performed. However, the present invention is not limited thereto. For example, the present invention may be applied to a case where the first measurement unit 2 is configured to measure the blood cells similarly to the above-mentioned embodiment, the second measurement unit 3 is configured to measure the coagulation and fibrinolytic ability of the blood, and the sample container measured by the first measurement unit 2 and the sample container measured by the second measurement unit 3 are mixed in the sample rack L. In this case, the sample processing apparatus 1 may be configured such that when the sample container T of the sample rack L which is positioned at the first sample container take-out/returning position 43a is taken out, the sample rack L is transported to the second sample container take-out/returning position 43b, and as a process for another sample container T accommodated in the sample rack L, the sample container T is not taken out from the sample rack L but an aspiration pipette is inserted into the sample container T so as to aspirate the sample.

In addition, in the above-mentioned embodiment, the configuration has been described such that the single computer 5a performs all the processes of the computer program 54a. However, the present invention is not limited thereto. For example, the configuration may employ a distributed system in which the process similar to the above-mentioned computer program 54a is distributed by plural apparatuses (computers) so as to be performed.

In addition, in the above-mentioned embodiment, the configuration has been described such that the sample is transported to the two measurement units 2 and 3 provided in the single sample processing apparatus 1 by the sample transport unit 4. However, the present invention is not limited thereto. For example, it may be configured such that two independent measuring apparatuses, in which the sample transport units are provided respectively, are provided, the sample transport units are connected to each other so as to form one transport line, and while the sample container is being taken in at least one measuring apparatus, the sample rack is transported to each measuring apparatus by the transport line, and the sample rack L is transported so as to carry out the process on the other sample container.

In addition, in the above-mentioned embodiment, the information processing unit 5 performs the obtaining process of the measuring order of the sample and the sample transport controlling process of the sample processing unit 4. However, the present invention is not limited thereto. For example, the obtaining process of the measuring order of the sample and the sample transport controlling process of the sample processing unit 4 may be performed by separated controlling sections.

In addition, in the above-mentioned embodiment, the sample container which is taken out from the sample rack L for the aspiration at the sample container take-out/returning position is returned to the sample rack L at the sample container take-out/returning position. However, the present invention is not limited thereto. For example, the returning position of the sample container which is taken out from the sample rack L may be a different position from the sample container take-out/returning position. Therefore, the take-out of the sample container from the same sample rack L can be performed in parallel with the returning of the sample container to the sample rack L, so that the sample processing capability can be further increased.

In addition, in the above-mentioned embodiment, the sample container which is taken out from the sample rack L for the aspiration at the sample container take-out/returning position is returned to the same sample rack L. However, the present invention is not limited thereto. For example, the sample container which is taken out from the sample rack L may be returned to a different sample rack L.

In addition, in the above-mentioned embodiment, the take-out of the sample container from the sample rack L and the returning of the sample container to the sample rack L is performed by the same mechanism. However, the present invention is not limited thereto. For example, the take-out and the returning may be performed by plural mechanisms different from each other (for example, an take-out hand and a returning hand).

What is claimed is:

1. A sample processing apparatus comprising:
   an aspiration section configured to aspirate a sample from a sample container;
   a sample container take-out/returning section configured to take out a sample container containing a sample which is to be aspirated by the aspiration section from a sample rack holding a plurality of sample containers, and to return the sample container from which the sample has been aspirated by the aspiration section to the sample rack;
a sample processing section configured to process the sample aspirated by the aspiration section;
a transport section configured to transport the sample rack to a take-out position to take out a sample container from the sample rack by the sample container take-out/returning section, to a processing position to perform a predetermined process on a sample container held by the sample rack, and to a returning position to return a sample container to the sample rack by the sample container take-out/returning section; and
a transport controller comprising a memory having stored thereon a program that, when executed by the transport controller, the transport controller controls the transport section to
transport the sample rack to the take-out position to take out one sample container from the sample rack by the sample container take-out/returning section;
transport the sample rack to the processing position to perform the predetermined process on another sample container held by the sample rack when the one sample container has been taken out from the sample rack by the sample container take-out/returning section; and
transport the sample rack to the returning position to return the one sample container to the sample rack by the sample container take-out/returning section after the predetermined process has been performed on the another sample container,
wherein the processing position is a position different from the take-out position.

2. The sample processing apparatus according to claim 1, wherein, when the transport controller executes the program, the transport controller determines whether or not the take-out/returning section is ready to take out a sample container from the sample rack, and controls the transport section to transport the sample rack to the take-out position when it has been determined that the sample container take-out/returning section is ready to take out the sample container from the sample rack.

3. The sample processing apparatus according to claim 1, further comprising a stirring section configured to stir the sample in the sample container which has been taken out from the sample rack by the sample container take-out/returning section,
wherein the aspiration section aspirates the sample stirred by the stirring section from the sample container.

4. The sample processing apparatus according to claim 1, further comprising a sample container detecting section configured to detect a sample container in the sample rack which has been transported to the processing position,
wherein the predetermined process includes detecting the another sample container in the sample rack by the sample container detecting section.

5. The sample processing apparatus according to claim 1, wherein each of the plurality of sample containers held by the sample rack includes an identifier in which identification information to identify a sample is recorded,
wherein the sample processing apparatus further comprises an identification information obtaining section configured to obtain identification information from an identifier of a sample container held by the sample rack which has been transported to the processing position, and wherein the predetermined process includes obtaining identification information of the another sample container by the identification information obtaining section.

6. The sample processing apparatus according to claim 1, further comprising:
a second aspiration section configured to aspirate a sample from a sample container;
a second sample container take-out/returning section configured to take out a sample container from the sample rack which is positioned at the processing position, and to return the sample container, from which a sample has been aspirated by the second aspiration section, to the sample rack; and
a second sample processing section configured to process the sample aspirated by the second aspiration section,
wherein the predetermined process includes taking out the another sample container from the sample rack by the second sample container take-out/returning section.

7. The sample processing apparatus according to claim 1, further comprising:
a second aspiration section configured to aspirate a sample from a sample container held by the sample rack which is positioned at the processing position; and
a second sample processing section configured to process the sample aspirated by the second aspiration section,
wherein the predetermined process includes aspirating a sample from the another sample container by the second aspiration section.

8. The sample processing apparatus according to claim 1, wherein the sample processing section measures the sample aspirated by the aspiration section.

9. The sample processing apparatus according to claim 1, wherein the take-out position and the processing position are provided on a transport path of the sample rack by the transport section.

10. The sample processing apparatus according to claim 1, wherein the take-out position is same as the returning position.

11. The sample processing apparatus according to claim 1, wherein the sample container take-out/returning section includes a grasping section configured to grasp a sample container, and performs taking out a sample container from the sample rack positioned at the take-out position and returning the sample container to the sample rack by using the grasping section.

12. The sample processing apparatus according to claim 1, wherein the take-out position and the returning position are different from each other.

13. The sample processing apparatus according to claim 1, wherein the sample container take-out/returning section comprises:
a take-out section configure to take out the sample container from the sample rack positioned at the take-out position; and
a returning section configured to return the sample container to the sample rack positioned at the returning position.

14. The sample processing apparatus according to claim 1, wherein the sample is a biological sample which is collected from a living body.

15. A sample processing apparatus comprising:
an aspiration section configured to aspirate a sample from a sample container;
a sample container take-out/returning section configured to take out a sample container containing a sample to be aspirated by the aspiration section from a sample rack holding a plurality of sample containers, and to return the sample container from which the sample has been aspirated by the aspiration section to the sample rack;

a sample processing section configured to process the sample aspirated by the aspiration section;

a sample container detecting section configured to detect a sample container in the sample rack which has been transported to a detecting position;

a transport section configured to transport the sample rack to a take-out position to take out a sample container from the sample rack by the sample container take-out/returning section, to the detecting position and to a returning position to return a sample container to the sample rack by the sample container take-out/returning section; and a transport controller comprising a memory having stored thereon a program that, when executed by the transport controller, the transport controller controls the transport section to transport the sample rack to the take-out position to take out one sample container from the sample rack by the sample container take-out/returning section;

transport the sample rack to the detecting position to detect another sample container held by the sample rack by the sample container detecting section when the one sample container has been taken out from the sample rack by the sample container take-out/returning section; and transport the sample rack to the returning position to return the one sample container to the sample rack by the sample container take-out/returning section after the another sample container has been detected by the sample container detecting section.

16. The sample processing apparatus according to claim 15, wherein each of the plurality of sample containers held by the sample rack includes an identifier in which identification information to identify a sample is recorded, wherein the sample processing apparatus further comprises an identification information obtaining section configured to obtain identification information from an identifier of a sample container held by the sample rack which has been transported to an identification information obtaining position, wherein after the another sample container is detected, the transport controller configured to control the transport section to transport the sample rack to the identification information obtaining position to obtain identification information of the another sample container by the identification information obtaining section.

17. The sample processing apparatus according to claim 15, wherein, when the transport controller executes the program, the transport controller determines whether or not the take-out/returning section is ready to take out a sample container from the sample rack, and controls the transport section to transport the sample rack to the take-out position when it has been determined that the sample container take-out/returning section is ready to take out the sample container from the sample rack.

18. The sample processing apparatus according to claim 15, further comprising a stirring section configured to stir the sample in the sample container which has been taken out from the sample rack by the sample container take-out/returning section, wherein the aspiration section aspirates the sample stirred by the stirring section from the sample container.

19. The sample processing apparatus according to claim 15, wherein the take-out position and the detecting position are provided on a transport path of the sample rack by the transport section.

20. A sample processing method of a sample processing apparatus comprising an aspiration section, a sample container take-out/returning section, a sample processing section, a transport section, and a transport controller, the sample processing method comprising:

transporting, by the transport section, a sample rack holding a plurality of the sample containers, each sample container containing a sample, to a take-out position;

taking out, by the sample container take-out/returning section, a first sample container from among the plurality of sample containers held by the sample rack positioned at the take-out position, the first sample container containing a sample which is to be aspirated;

transporting, by the transport section, the sample rack to a processing position for performing a predetermined process on a second container from among the plurality of sample containers held by the sample rack when the first sample container has been taken out from the sample rack;

performing, by the sample processing section, the predetermined process on the second sample container;

aspirating, by the aspiration section, the sample from the first sample container which has been taken out from the sample rack;

processing, by the sample processing section, the aspirated sample;

transporting, by the transport section, the sample rack to a returning position; and returning, by the sample container take-out/returning section, the first sample container, from which the sample has been aspirated, to the sample rack which is positioned at the returning position, wherein the processing position is a position different from the take-out position.

21. The sample processing method of claim 20 further comprising:

determining, by the transport controller, whether or not the take-out/returning section is ready to take out a sample container from the sample rack; and transporting, by the transport section, the sample rack to the take-out position when it has been determined that the sample container take-out/returning section is ready to take out the sample container from the sample rack.

* * * * *